US007537938B2

(12) United States Patent
Kirakossian et al.

(10) Patent No.: US 7,537,938 B2
(45) Date of Patent: *May 26, 2009

(54) BIOMARKER DETECTION IN CIRCULATING CELLS

(75) Inventors: Hrair Kirakossian, San Jose, CA (US); Thomas Klopack, Encinitas, CA (US); Sharat Singh, Los Altos, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 78 days.

This patent is subject to a terminal disclaimer.

(21) Appl. No.: 10/765,773

(22) Filed: Jan. 26, 2004

(65) Prior Publication Data

US 2004/0157271 A1     Aug. 12, 2004

Related U.S. Application Data

(60) Continuation-in-part of application No. 10/154,042, filed on May 21, 2002, now Pat. No. 7,255,999, and a continuation-in-part of application No. 10/420,549, filed on Apr. 18, 2003, which is a division of application No. 09/698,849, filed on Oct. 27, 2000, now Pat. No. 6,627,400, which is a continuation-in-part of application No. 09/602,586, filed on Jun. 21, 2000, now Pat. No. 6,514,700, which is a continuation-in-part of application No. 09/561,579, filed on Apr. 28, 2000, now Pat. No. 6,682,887.

(51) Int. Cl.
G01N 33/553 (2006.01)
G01N 33/53 (2006.01)

(52) U.S. Cl. ............. 436/526; 436/518; 436/501; 436/538; 436/540; 435/6; 435/7.1; 435/7.2; 435/7.7; 435/7.95

(58) Field of Classification Search ............ 436/518, 436/526, 538, 540; 435/6, 7.1, 7.2, 7.7, 7.95, 435/7.72
See application file for complete search history.

(56) References Cited

U.S. PATENT DOCUMENTS 4,274,240 A     6/1981   Soum ....................... 52/583

(Continued)

FOREIGN PATENT DOCUMENTS

DE           4307736 A1      9/1993

(Continued)

OTHER PUBLICATIONS

Adam et al., "Photooxygenation (Singlet Oxygen) of Tetrathioethylenes", Journal of the American Chemical Society, vol. 94:4, 1972, pp. 1206-1208.

(Continued)

*Primary Examiner*—Mark L Shibuya
*Assistant Examiner*—Pensee T Do
(74) *Attorney, Agent, or Firm*—Fenwick & West LLP

(57) ABSTRACT

A method is provided for detecting biomarkers in rare circulating cells by forming an enriched population of cells immunomagnetically followed by biomarker detection using binding compounds having releasable molecular tags. Preferably, biomarkers comprising one or more protein-protein complexes are detected in circulating cancer cells metastasized from a solid tumor. In the presence of biomarkers, the molecular tags of the binding compounds are released and separated from the assay mixture for detection and/or quantification.

11 Claims, 10 Drawing Sheets

U.S. PATENT DOCUMENTS

| | | | | |
|---|---|---|---|---|
| 4,331,590 A | | 5/1982 | Bocuslaski | 260/112 B |
| 4,375,407 A | | 3/1983 | Kronick | 209/223 |
| 4,452,773 A | | 6/1984 | Molday | 436/529 |
| 4,650,750 A | | 3/1987 | Giese | 435/7 |
| 4,675,300 A | | 6/1987 | Zare | 436/172 |
| 4,709,016 A | | 11/1987 | Giese | 530/389 |
| 4,780,421 A | | 10/1988 | Kameda | 436/518 |
| 5,057,412 A | | 10/1991 | Rabin | 435/6 |
| 5,186,827 A | * | 2/1993 | Liberti et al. | 210/222 |
| 5,231,178 A | | 7/1993 | Holtz et al. | |
| 5,254,469 A | | 10/1993 | Warren, III | 435/188 |
| 5,262,176 A | | 11/1993 | Palmacci et al. | 424/9 |
| 5,324,401 A | | 6/1994 | Yeung | 204/180.1 |
| 5,340,716 A | | 8/1994 | Ullman | 435/6 |
| 5,360,819 A | | 11/1994 | Giese | 514/538 |
| 5,432,054 A | * | 7/1995 | Saunders et al. | 435/2 |
| 5,445,970 A | | 8/1995 | Rohr | 436/526 |
| 5,470,705 A | | 11/1995 | Grossman | 435/6 |
| 5,494,793 A | | 2/1996 | Schindele | 435/6 |
| 5,508,164 A | | 4/1996 | Kausch et al. | 435/6 |
| 5,514,340 A | * | 5/1996 | Lansdorp et al. | 422/101 |
| 5,514,543 A | | 5/1996 | Grossman | 435/6 |
| 5,516,636 A | | 5/1996 | McCapra | 435/6 |
| 5,516,931 A | | 5/1996 | Giese | 560/59 |
| 5,536,834 A | | 7/1996 | Singh | 544/98 |
| 5,560,811 A | | 10/1996 | Briggs | 204/451 |
| 5,565,324 A | | 10/1996 | Still | 435/6 |
| 5,567,292 A | | 10/1996 | Madabhushi | 204/451 |
| 5,571,894 A | * | 11/1996 | Wels et al. | 530/387.3 |
| 5,573,906 A | | 11/1996 | Bannwarth | 435/6 |
| 5,578,498 A | | 11/1996 | Singh | 436/518 |
| 5,580,732 A | | 12/1996 | Grossman | 435/6 |
| 5,602,273 A | | 2/1997 | Giese | 560/60 |
| 5,604,104 A | | 2/1997 | Giese | 435/7.1 |
| 5,610,020 A | | 3/1997 | Giese | 435/7.1 |
| 5,616,719 A | | 4/1997 | Davalian | 546/334 |
| 5,624,800 A | | 4/1997 | Grossman | 435/6 |
| 5,646,001 A | * | 7/1997 | Terstappen et al. | 435/7.21 |
| 5,648,222 A | * | 7/1997 | Tse et al. | 435/7.23 |
| 5,650,270 A | | 7/1997 | Giese | 435/6 |
| 5,665,582 A | | 9/1997 | Kausch et al. | 434/181 |
| 5,691,151 A | | 11/1997 | Braun | 435/7.2 |
| 5,691,208 A | | 11/1997 | Miltenyi et al. | 436/526 |
| 5,703,222 A | | 12/1997 | Grossman | 536/24.3 |
| 5,705,622 A | | 1/1998 | McCapra | 536/23.1 |
| 5,709,994 A | | 1/1998 | Pease | 435/4 |
| 5,719,028 A | | 2/1998 | Dahlberg | 435/6 |
| 5,721,099 A | | 2/1998 | Still | 435/6 |
| 5,723,591 A | | 3/1998 | Livak | 536/22.1 |
| 5,756,726 A | | 5/1998 | Hemmi | 540/474 |
| 5,763,602 A | | 6/1998 | Li | 540/128 |
| 5,766,481 A | | 6/1998 | Zambias | 210/656 |
| 5,777,096 A | | 7/1998 | Grossman | 536/24.3 |
| 5,789,172 A | | 8/1998 | Still | 435/6 |
| 5,795,470 A | * | 8/1998 | Wang et al. | 210/222 |
| 5,807,675 A | | 9/1998 | Davalian | 435/6 |
| 5,807,682 A | | 9/1998 | Grossman | 435/6 |
| 5,811,239 A | | 9/1998 | Frayne | 435/6 |
| 5,843,655 A | | 12/1998 | McGall | 435/6 |
| 5,843,666 A | | 12/1998 | Akhavan-Tafti | 435/6 |
| 5,846,839 A | | 12/1998 | Gallop | 436/518 |
| 5,849,878 A | | 12/1998 | Cantor | 530/391.9 |
| 5,851,770 A | | 12/1998 | Babon | 435/6 |
| 5,874,213 A | | 2/1999 | Cummins | 435/6 |
| 5,876,930 A | | 3/1999 | Livak | 435/6 |
| 5,916,426 A | | 6/1999 | Madabhushi | 204/451 |
| 5,952,654 A | | 9/1999 | Giese | 250/288 |
| 5,958,202 A | | 9/1999 | Regnier | 204/451 |
| 5,985,153 A | * | 11/1999 | Dolan et al. | 210/695 |
| 5,986,076 A | | 11/1999 | Rothschild | 536/22.1 |
| 5,989,871 A | | 11/1999 | Grossman | 435/91.1 |
| 5,993,665 A | * | 11/1999 | Terstappen et al. | 210/695 |
| 5,994,069 A | | 11/1999 | Hall et al. | |
| 5,998,140 A | | 12/1999 | Dervan | 435/6 |
| 5,998,224 A | | 12/1999 | Rohr et al. | 435/526 |
| 6,001,567 A | | 12/1999 | Brow | 435/6 |
| 6,001,579 A | | 12/1999 | Still | 435/7.1 |
| 6,027,890 A | | 2/2000 | Ness | 435/6 |
| 6,045,676 A | | 4/2000 | Mathies | 204/603 |
| 6,048,515 A | | 4/2000 | Kresse et al. | 424/9.322 |
| 6,090,947 A | | 7/2000 | Dervan | 548/312.4 |
| 6,136,182 A | * | 10/2000 | Dolan et al. | 210/94 |
| 6,251,581 B1 | | 6/2001 | Ullman | 435/4 |
| 6,312,893 B1 | | 11/2001 | Van Ness | 435/6 |
| 6,322,980 B1 | | 11/2001 | Singh | 435/6 |
| 6,331,530 B1 | | 12/2001 | Breslow | 514/58 |
| 6,335,201 B1 | | 1/2002 | Allbritton | 436/63 |
| 6,346,384 B1 | | 2/2002 | Pollner | 435/6 |
| 6,346,529 B1 | | 2/2002 | Floyd | 514/226.2 |
| 6,361,749 B1 | * | 3/2002 | Terstappen et al. | 422/186.01 |
| 6,365,362 B1 | * | 4/2002 | Terstappen et al. | 435/7.23 |
| 6,368,874 B1 | | 4/2002 | Gallop | 436/518 |
| 6,558,928 B1 | | 5/2003 | Landegren | |
| 6,627,400 B1 | * | 9/2003 | Singh et al. | 435/6 |
| 6,649,351 B2 | | 11/2003 | Matray et al. | |
| 6,660,159 B1 | * | 12/2003 | Terstappen et al. | 210/94 |
| 6,709,818 B1 | * | 3/2004 | Nelson et al. | 435/6 |
| 6,770,439 B2 | | 8/2004 | Singh et al. | |
| 6,790,366 B2 | * | 9/2004 | Terstappen et al. | 210/695 |
| 6,815,212 B2 | * | 11/2004 | Ness et al. | 436/173 |
| 6,949,347 B2 | | 9/2005 | Singh et al. | |
| 7,105,308 B2 | | 9/2006 | Chan-Hui et al. | |
| 7,135,300 B2 | | 11/2006 | Chan-Hui et al. | |
| 7,160,735 B2 | | 1/2007 | Dehlinger et al. | |
| 7,358,052 B2 | | 4/2008 | Singh | |
| 2001/0049105 A1 | | 12/2001 | Singh et al. | |
| 2002/0037542 A1 | | 3/2002 | Allbritton et al. | 435/7.23 |
| 2002/0045178 A1 | | 4/2002 | Cantor et al. | |
| 2002/0064779 A1 | | 5/2002 | Landegren et al. | |
| 2002/0098478 A1 | | 7/2002 | Wold | |
| 2002/0128465 A1 | | 9/2002 | Lyamichev | 536/24.3 |
| 2004/0229380 A1 | | 11/2004 | Chan-Hui et al. | |

FOREIGN PATENT DOCUMENTS

| | | |
|---|---|---|
| EP | 0 484 027 A1 | 5/1992 |
| EP | 0552931 B1 | 5/2000 |
| WO | WO 93/06121 | 4/1993 |
| WO | WO 96/24061 | 8/1996 |
| WO | WO 97/17467 A1 | 5/1997 |
| WO | WO 97/27325 | 7/1997 |
| WO | WO 97/27327 | 7/1997 |
| WO | WO 97/28275 | 8/1997 |
| WO | WO 98/01533 | 1/1998 |
| WO | WO 98/15830 | 4/1998 |
| WO | WO 99/05319 | 2/1999 |
| WO | WO 99/13108 | 3/1999 |
| WO | WO 99/42838 | 8/1999 |
| WO | WO 99/64519 | 12/1999 |
| WO | WO 00/16087 A1 | 3/2000 |
| WO | WO 00/56925 | 9/2000 |
| WO | WO 00/66607 | 11/2000 |
| WO | WO 02/29109 A2 | 4/2002 |
| WO | WO 02/083954 A1 | 10/2002 |
| WO | WO 02/097112 A2 | 12/2002 |

OTHER PUBLICATIONS

Adam et al., "Photooxygenation of Vinyl Sulfides: Substituent Effects on the [2+2] Cycloaddition versus Schenck Ene Reaction Modes", Tetrahedron Letters, vol. 36, No. 43, Pergamon Press 1995, pp. 7853-7854.

Ando et al., "Photosensitized Oxygenation of Vinylic Sulphides", J.C.S. Chem. Comm., 1972, pp. 477-478.

Ando et al., "Singlet Oxygen Reaction—II Alkylthiosubstituted Ethylene[1]", Tetrahedron, vol. 29, Pergamon Press 1973, pp. 1507-1513.

Ando et al., "Singlet Oxygen Reaction. III. Solvent and Temperature Effects on the Photosensitized Oxygenation of Vinyl Sulfides and Vinyl Ethers", Journal of the American Chemical Society, vol. 96:21, 1974, pp. 6766-6768.

Ando et al., "Singlet Oxygen Reaction. IV. Photooxygenation of Enamines Involving a Two-Step Cleavage of a 1, 2-Dioxetane Intermediate[1]", Journal of American Chemical Society, vol. 97:17, 1975, pp. 5028-5029.

Ando et al., "Singlet Oxygen Reaction V. Ring Size Effects on the Decomposition of Sulfur Substituted 1, 2-Dioxetane[1]", Tetrahedron Letters, No. 47, Pergamon Press 1975, pp. 4127-4130.

Brenner et al., "Encoded Combinatorial Chemistry", Proc. Natl. Acad. Sci. USA, vol. 89, 1992, pp. 5381-5383.

Fitch et al., "Improved Methods for Encoding and Decoding Dialkylamine-Encoded Combinatorial Libraries", J. Comb. Chem., 1, 1999, pp. 188-194.

Giese, "Electrophoric Release Tags: Ultrasensitive Molecular Labels Providing Multiplicity", Trends in Analytical Chemistry, vol. 2, No. 7, 1983, pp. 166-168.

Hacia et al., "Detection of Heterozygous Mutations in BRCA1 Using High Density Oligonucleotide Arrays and Two-Colour Fluorescence Analysis", Nature Genetics, vol. 14, 1996, pp. 441-447.

Haff et al., "Multiplex Genotyping of PCR Products with MassTag-Labled Primers", Nucleic Acids Research, vol. 25, No. 18, 1997, pp. 3749-3750.

Holland et al., "Detection of Specific Polymerase Chain Reaction Product by Utilizing the 5' → 3' Exonuclease Activity of *Thermus Aquaticus* DNA Polymerase", Proc. Natl. Acad. Sci. USA, vol. 88, 1991, pp. 7276-7280.

Houghten et al., "Human β -Endorphin: Synthesis and Characterization of Analogs Iodinated and Tritiated at Tryosine Residues 1 and 27", Int. J. Peptide Protein Res., vol. 16, 1980, pp. 311-320.

Kochevar et al., "Photosensitized Production of Singlet Oxygen", Methods in Enzymology, vol. 319, 2000, pp. 20-29.

Lee et al., "Allelic Discrimination by Nick-Translation PCR with Fluorogenic Probes", Nucleic Acids Research, vol. 21, No. 16, 1993, pp. 3761-3766.

Liu et al., "Capillary Electrochromatography-laser-induced Fluorescence Method for Separation and Detection of Dansylated Dialkylamine Tags in Encoded Combinatorial Libraries", Journal of Chromatorgraphy, Art. 924, 2001, pp. 323-329.

Lu et al., "Polymerizable Fab' Antibody Fragments for Targeting of Anticancer Drugs", Nature Biotechnology, vol. 17, 1999, pp. 1101-1104.

Lum et al., "Ability of Specific Monoclonal Antibodies and Conventional Antisera Conjugated to Hematoporphyrin to Label and Kill Selected Cell Lines Subsequent to Light Activation", Cancer Research, vol. 45, 1985, pp. 4380-4386.

Marglin et al., "Chemical Synthesis of Peptides and Proteins", Art. 739, 1970, pp. 841-866.

Marino et al., "Characterization of Mitochondrial DNA Using Low-Stringency Single Specific Primer Amplification Analyzed by Laser Induced Fluoroscence—Capillary Electrophoresis", Electrophoresis, vol. 17, 1996, pp. 1499-1504.

Matthews et al., "Analytical Strategies for the Use of DNA Probes", Analytical Biochemistry, vol. 169, 1988, pp. 1-25.

Merrifield, "Solid Phase Peptide Synthesis. I. The Synthesis of a Tetrapeptide", Synthesis of a Tetrapeptide, vol. 85, 1963, pp. 2149-2154.

Ni et al., "Versatile Approach to Encoding Combinatorial Organic Synthesis Using Chemically Robust Secondary Amine Tags", J. Med. Chem., vol. 39, 1996, pp. 1601-1608.

Olejnik et al., "Photocleavable Affinity Tags for Isolation and Detection of Biomolecules", Methods in Enzymology, vol. 291, 1998, pp. 135-154.

Oseroff et al., "Antibody-Targeted Photolysis: Selective photodestruction of Human T-Cell Leukemia Cells Using Monoclonal Antibody-Chlorin e6 Conjugates", Proc. Natl. Acad. Sci. USA, vol. 83, 1986, pp. 8744-8748.

Posewitz et al., "Immobilized Gallium(III) Affinity Chromatography of Phosphopeptides", Anal. Chem., vol. 71, 1999, pp. 2883-2892.

Rakestraw et al., "Antibody-Targeted photolysis: In vitro Studies with Sn(IV) Chlorin e6 Covalently Bound to Monoclonal Antibodies Using a Modified Dextran Carrier", Proc. Natl. Acad. Sci. USA, vol. 87, 1990, pp. 4217-4221.

Da Ros et al., "DNA-Photocleavage Agents", Current Pharmaceutical Design, vol. 7, 2001, pp. 1781-1821.

Ross et al., "Discrimination of Single-Nucleotide Polymorphisms in Human DNA Using Peptide Nucleic Acid Probes Detected by MALDI-TOF Mass Spectrometry", Anal. Chem., vol. 69, 1997, pp. 4197-4202.

Sharman et al., "Role of Activated Oxygen Species in Photodynamic Therapy", Methods in Enzymology, vol. 319, 2000, pp. 376-400.

Still, "Discovery of Sequence-Selective Peptide Binding by Synthetic Receptors Using Encoded Combinatorial Libraries", Acc. Chem. Res., vol. 29, 1996, pp. 155-163.

Strong, "Antibody-Targeted Photolysis", Annals New York Academy of Sciences, vol. 745, 1994, pp. 297-320.

Ullman et al., "Luminescent Oxygen Channeling Immunoassay: Measurement of Particle Binding Kinetics by Chemiluminescence", Proc. Natl. Acad. Sci. USA, vol. 91, 1994, pp. 5426-5430.

Wang et al., "Large-Scale Identification, Mapping, and Genotyping of Single-Nucleotide Polymorphisms in the Human Genome", Science, vol. 280, 1998, pp. 1077-1082.

Wasserman et al., "Enamine-Single Oxygen Reactions. α-Diketones from Intermediate Amino Dioxetanes", Tetrahedron Letters, No. 21, 1975, pp. 1735-1738.

Wetmur, "DNA Probes: Applications of the Principles of Nucleic Acid Hybridization", Critical Reviews in Biochemistry and Molecular Biology, vol. 26, 1991, pp. 227-259.

White, "The Future of PCR Technology: Diversification of Technologies and Applications", Tibtech, vol. 14, 1996, pp. 478-483.

Wöhrle, "Porphyrins, Phthalocyanines, and Naphthalocyanines for Various Processes fo Visible Light Driven Conversion Processes", Chimia, vol. 45, 1991, pp. 307-310.

Woolley et al., "Functional Integration of PCR Amplification and Capillary Electrophoresis in a Microfabricated DNA Analysis Device", Anal. Chem., vol. 68, 1996, pp. 4081-4086.

Yarmush et al., "Antibody Targeted Photolysis", Critical Reviews in Therapeutic Drug Carrier Systems, vol. 10, 1993, pp. 197-252.

Yemul et al., "Selective Killing of T Lymphocytes by Phototoxic Liposomes", Proc. Natl. Acad. Sci. USA, vol. 84, 1987, pp. 246-250.

Zaklika et al., "Mechanisms of 1,2-Dioxetane Decomposition: The Role of Electron Transfer", Photochemistry and Photobiology, vol. 30, 1979, pp. 35-44.

X.C. Hu et al., "Immunomagnetic umor Cell Enrichment is Promising in Detecting Circulatng Breast Cancer Cells" Oncoloby, 2003;64: 160-165.

Moreno et al, "Changes in Circulating Carcinoma Cells in Pateints with Metastatic Prostate Cancer Correlate with Disease Status", Adult Uroloby, 58 (3), 2001.

Nam et al, "Nanoparticle-based Bio-bar Codes for the Ultrasensitive Detection of Proteins", Science, vol. 301, Sep. 26, 2003.

Zigeuner et al, "Isolation of Circulating Cancer Cells From Whole Blood by Immunomagnetic Cell Enrichment and Unenriched Immunocytochemistry in Vitro", The Journal of Urology, Vo. 169, Feb. 2003, 701-705.

Ghossein et al., "Molecular Detection and Charaterization of Circulating Tumor Cells and Micrometastases in Prostatic, Urothelial, and Renal Cell Carcinomas" Seminars in Surgical Oncology, 2001, 20: 304-311.

Stefan Miltenyi et al., "High Gradient Magnetic Cell Separation with MCCS[1]", Cytometry, 11: 231-238, (1990).

W. Schutt et al., "Applications of Magnetic Targeting in Diagnosis and Therapy-Possibilities and Limitations: A Mini-Review", Hybridoma, vol. 16, No. 1, 1997.

Andreas Radbruch et al, "High-Gradient Magnetic Cell Sorting", Methods in Cell Biology, vol. 42, 1994.

Jeffrey J. Chalmers, et al, "Theoretical Analysis of Cell Separation Bsed on Cell Surface marker Density", Biotechnology and Bioengineering, Vo. 59, No. 1, Jul. 5, 1998, 11-20.

Masayui Nakamura et al, "Separatio of Breast Cancer Cell Line from Human Blood Using a Quadrupole Magnetic Flow Sorter", Biotechnol Prog., 2001, Vo. 17, No. 6.

Bong Kyung Shin, "Hroteomics Approaches to Uncover the Repertoire of Circulating Biomarkers for Breast Cancer", Journal of Mammary Gland Biology and Neoplsia, vol. 7, No. 4, Oct. 2002.

Emilian Racila, et al, "Detection and Charaterization of Carcinoma Cells in the Blood", Proc. Natl. Acad. Sci. USA, vol. 95, pp. 4589-4594, Apr. 1998.

David Sidransky, "Emerging Molecular Markers of Cancer", Nature Review/Cancer, vol. 2, Mar. 2002, 211-219.

Ivo Safarik, et al, "Use of Magnetic Techniques for the Isolation of Cells", Journal of Chromatography B., 722 (1999) 33-53.

Autiero et al., "Role of PIGF in the Intra- and Intermolecular Cross Talk Between VEGF Receptors Fit1 and Fik1," Nature Medicine, Jun. 8, 2003, pp. 936-943, vol. 9.

Burmer, G.C. et al., Frequency and Spectrum of c-Ki-*ras* Mutations in Human Sporadic Colon Carcinoma, Carinomas Arising in Ulcerative Colitis, and Pancreatic Adenocarcinoma, Environmental Health Perspectives, 1991, pp. 27-31, vol. 93.

Busken, C. et al., "Adenocarcinomas of the Gastro-Esophageal Junction: A Comparative Study of the Gastric Cardia and the Esophagus with Respect to Cycloxygenase-2 Expression," Digestive Disease Week Abstracts and Itinerary Planner, 2003, Abstract No. 850.

Drexler, H.G. et al., "Recent Results on the Biology of Hodgkin and Reed-Stemberg Cells, II. Continuous Cell Lines," Leukemia and Lymphoma, 1993, pp. 1-25, vol. 9.

Embleton, M.J. et al., "Monoclonal Antibodies to Osteogenic Sacroma Antigens," Immunol. Ser., 1984, pp. 181-207, vol. 23.

European Supplementary Search Report, European Application EP 03815205.4, Jan. 10, 2008, 6 pages.

European Supplementary Search Report, European Application EP03746104.3, Jun. 1, 2007, 2 pages.

Hsu, T.C., "Karyology of Cells in Culture," Tissue Culture Methods and Applications, Kruse and Patterson, Eds., Academic Press, N.Y., 1973, p. 764.

Kunkel, P. et al., "Expression and Localization of Scatter Factor/Hepatocyte Growth Factor in Human Astrocytomas," Neuro-Oncology, Apr. 2001, pp. 82-88, vol. 3, No. 2.

Montesano, R. et al., "Genetic Alterations in Esophageal Cancer and Their Relevance to Etiology and Pathogenesis: A Review," Intl. J. Cancer, 1996, pp. 225-235, vol. 69, No. 3.

Slamon, D.J. et al., "Human Breast Cancer: Correlation of Relapse and Survival and Amplification of the HER-2/*neu* Oncogene," Science, Jan. 9, 1987, pp. 177-182, vol. 235.

Tian, J. et al., "The Expression of Native and Cultured RPE Grown on Difference Matrices," Physiol. Genomics, Feb. 24, 2004, pp. 170-182, vol. 17.

Tockman, M.S. et al., "Considerations in Bringing a Cancer Biomarker to Clinical Application," Cancer Research, May 1, 1992, pp. 2711s-2718s, vol. 52.

Van Dyke, D. et al., "Monosomy 21 in Hematologic Diseases," Cancer Genetics and Cytogenetics, 2003, pp. 137-141, vol. 241.

Wathelet, M. et al., "Electrophereogram Comparison by Computer," Chemometrics and Intelligent Laboratory Systems, 1998, pp. 327-339, vol. 4.

Whitaker, G.B. et al., "Vascular Endothelial Growth Factor Receptor-2 and Neuropilin-1 Form a Receptor Complex That Is Responsible for the Differential Signaling Potency of $VEGF_{165}$ and $VEGF_{121}$," The Journal of Biological Chemistry, Jul. 6, 2001, pp. 25520-25531, vol. 276.

Wildi, S. et al., "Overexpression of Activin A in Stage IV Colorectal Cancer," Gut Online, Sep. 2001, pp. 409-471, vol. 49.

Zaslav, A.L. et al., "Significance of a Prenatally Diagnosed del(10)(q23)," American Journal of Medical Genetics, 2002, pp. 174-176, vol. 107.

Shinmura, K. et al., "8-Hydroxyguanine (7,8-dihydro-8-oxoguanine) DNA Glycosylase and AP Lyase Activities of hOGG1 Protein and Their Substrate Specificity," Mutation Research, 1997, pp. 75-82, vol. 385.

\* cited by examiner

BIOMARKER DETECTION IN CIRCULATING CELLS

RELATED APPLICATIONS

This is a continuation-in-part of U.S. patent application Ser. No. 10/154,042 filed 21 May 2002 now U.S. Pat. No. 7,255,999 and a continuation-in-part of U.S. patent application Ser. No. 10/420,549 filed 18 Apr. 2003, which is a divisional of U.S. patent application Ser. No. 09/698,849 filed 27 Oct. 2000 (now U.S. Pat. No. 6,627,400), which is a continuation-in-part of U.S. patent application Ser. No. 09/602,586 filed 21 Jun. 2000 (now U.S. Pat. No. 6,514,700), which is a continuation-in-part of U.S. application Ser. No. 09/561,579 filed 28 Apr. 2000 (now U.S. Pat. No. 6,682,887), all of which are incorporated by reference.

FIELD OF THE INVENTION

The present invention relates generally to a method of detecting antigens of circulating cells, and more particularly, to a method of detecting antigens of circulating cancer cells.

BACKGROUND OF THE INVENTION

A biomarker is a characteristic that is objectively measured and evaluated as an indicator of normal biological processes, pathogenic processes, or pharmacological responsees to a therapeutic intervention, Atkinson et al, Clin. Pharmacol. Ther., 69: 89-95 (2001). Biomarkers vary widely in nature, ease of measurement, and correlation with physiological states of interest, e.g. Frank et al, Nature Reviews Drug Discovery, 2: 566-580 (2003). It is believed that the development of new validated biomarkers will lead both to significant reductions in healthcare and drug development costs and to significant improvements in treatment for a wide variety of diseases and conditions. Thus, a great deal of effort has been directed to using new technologies to find new classes of biomarkers, e.g. Petricoin et al, Nature Reviews Drug Discovery, 1: 683-695 (2002).

In the area of cancer treatment, there is a particular need for sensitive assays for detecting cancer cells to guide treatment and to monitor the effects of such treatment, especially on metastasis or relapse. For example, the approach for determining the presence of circulating prostate tumor cells has been to test for the expression of messenger RNA of prostate specific antigen (PSA) in blood. This is being done through the laborious procedure of isolating all of the mRNA from a blood sample and performing reverse transcriptase PCR. Presently, however, no good correlation exists between the presence of such cells in blood and the ability to predict which patients are in need of vigorous treatment, Gomella, J of Urology. 158:326-337 (1997). It is noteworthy that PCR is difficult, if not impossible in many situations, to perform quantitatively, i.e., determine number of tumor cells per unit volume of biological sample. Additionally false positives are often observed using this technique. There is an added drawback which is that there is a finite and practical limit to the sensitivity of this technique based on the sample size examined. Typically, the test is performed on $10^5$ to $10^6$ cells purified away from interfering red blood cells. This corresponds to a practical lower limit of sensitivity of one tumor cell/0.1 ml of blood. Hence, there needs to be about 10 tumor cells in a ml of blood before signal is detectable. As a further consideration, tumor cells are often genetically unstable. Accordingly, cancer cells having genetic rearrangements and sequence changes may be missed in a PCR assay as the requisite sequence complementarity between PCR primers and target sequences can be lost.

A useful diagnostic test needs to be very sensitive and reliably quantitative. If a blood test can be developed where the presence of a single tumor cell can be detected in one ml of blood, that would correspond on average to 3000-4000 total cells in circulation. In innoculum studies for establishing tumors in animals, that number of cells can indeed lead to the establishment of a tumor. Further if 3000-4000 circulating cells represents 0.01% of the total cells in a tumor, then it would contain about $4\times10^7$ total cells. A tumor containing that number of cells would not be visible by any technique currently in existence. Hence, if tumor cells are shed in the early stages of cancer, a test with the sensitivity mentioned above should detect the cancer. If tumor cells are shed in some functional relationship with tumor size, then a quantitative test would be beneficial to assessing tumor burden. It is apparent that a method for identifying those cells in circulation with metastatic potential prior to establishment of a secondary tumor is highly desirable, particularly early on in a cancer. To appreciate the advantage such a test would have over conventional immunoassays, consider that a highly sensitive immunoassay has a lower limit of functional sensitivity of $10^{-17}$ moles. If one tumor cell can be captured from a ml of blood and analyzed, the number of moles of surface receptor, assuming 100,000 receptors per cell would be $10^{-19}$ moles. Since about 300 molecules can be detected on a cell such an assay would have a functional sensitivity on the order of $10^{-22}$ moles. To achieve that level of sensitivity in the isolation of such rare cells, and to isolate them in a fashion which does not compromise or interfere with their characterization is a formidable task.

In view of the above, a highly sensitive and reliable assay for detecting and quantifying the rare cell types, especially metastasized cancer cells, circulating in the blood would lead to improvements in diagnostics and patient treatment.

SUMMARY OF THE INVENTION

The present invention provides a rapid and efficient screening method for the characterization of not only tumor cells, but also rare cells, or other biological entities from biological samples, especially blood. The method described herein combines elements of immunomagnetic enrichment with the use of releasable molecular tags that are separated from an assay mixture for detection and quantification. Other means of enrichment such as density gradient centrifugation or panning or alteration of target cell density by appropriate labeling may also be utilized. According to a preferred embodiment, the method of the invention enables assaying whole blood for cancer staging, monitoring and screening. The sensitive nature of the assay facilitates the detection of residual disease, thus making it possible to monitor for cancer recurrence.

In one embodiment of the invention, a biological specimen, which comprises a mixed cell population suspected of containing the rare cell of interest is obtained from a patient. A sample is then prepared by mixing the biological specimen with magnetic particles which are coupled to a biospecific ligand specifically reactive with an antigen on the rare cell that is different from or not found on blood cells (referred to herein as a "capture antigen"), so that other sample components may be substantially removed. The sample is subjected to a magnetic field which is effective to separate cells labeled with the magnetic particles, including the rare cells of interest, if any are present in the specimen. The cell population so isolated is then analyzed using molecular tags conjugated to binding moieties specific for biomarkers to determine the presence and/or number of rare cells. In a preferred embodiment the magnetic particles used in this method are colloidal magnetic nanoparticles.

In another aspect of the invention, a method of the following steps is provided: (i) immunomagnetically isolating from a sample a subpopulation of cells containing a rare cell type by contacting the sample with one or more antibody compositions, each antibody composition being specific for a capture antigen and being attached to a magnetic particle; (ii) providing a binding compound for one or more biomarkers, each binding compound having one or more molecular tags releasably attached thereto, the one or more molecular tags of each different binding compound having a distinct separation characteristic so that molecular tags of each different binding compound form distinct peaks in a separation profile upon separation; (iii) combining with the subpopulation a binding compound for each of the plurality of biomarkers such that in the presence of a biomarker a complex is formed between each biomarker and the binding compound specific therefor; (iv) releasing the molecular tags of each binding compound forming such a complex; and (v) separating and identifying the released molecular tags to determine the one or more biomarkers in the sample.

In a further aspect of the present invention, a test kit is provided for screening a patient sample for the presence of circulating rare cells. The screening kit comprises: (i) coated, magnetic nanoparticles coupled, directly or indirectly, to a biospecific ligand, such as an antibody composition, that has affinity for a characteristic determinant, or capture antigen, on a rare cell; and (ii) one or more binding compounds, such that there is at least one binding compound specific for each biomarker of interest, each binding compound having one or more molecular tags, each molecular tag being attached by a cleavable linkage, and the molecular tags of each binding compound being distinguishable from those of every other binding compound by one or more physical and/or optical characteristics. The kits of the invention may contain reagents for diagnosing the type of the metastatic cancer cells in the circulation as well as the metastatic potential and aggressiveness of such cells. In this embodiment the kit contains the reagents recited above, yet also comprises additional antibody markers to facilitate cancer diagnosis.

The present invention provides a method of detecting or measuring biomarkers in an enriched population of rare circulating cells. The invention has several advantages over current techniques including, but not limited to, (1) separation and enrichment of a rare cell population from a complex population of biological cells, (2) the detection and/or measurement of molecular tags that are separated from an assay mixture provide greatly reduced background and a significant gain in sensitivity; and (3) the use of molecular tags that are specially designed for ease of separation and detection thereby providing convenient multiplexing capability.

DEFINITIONS

Figure 1A:
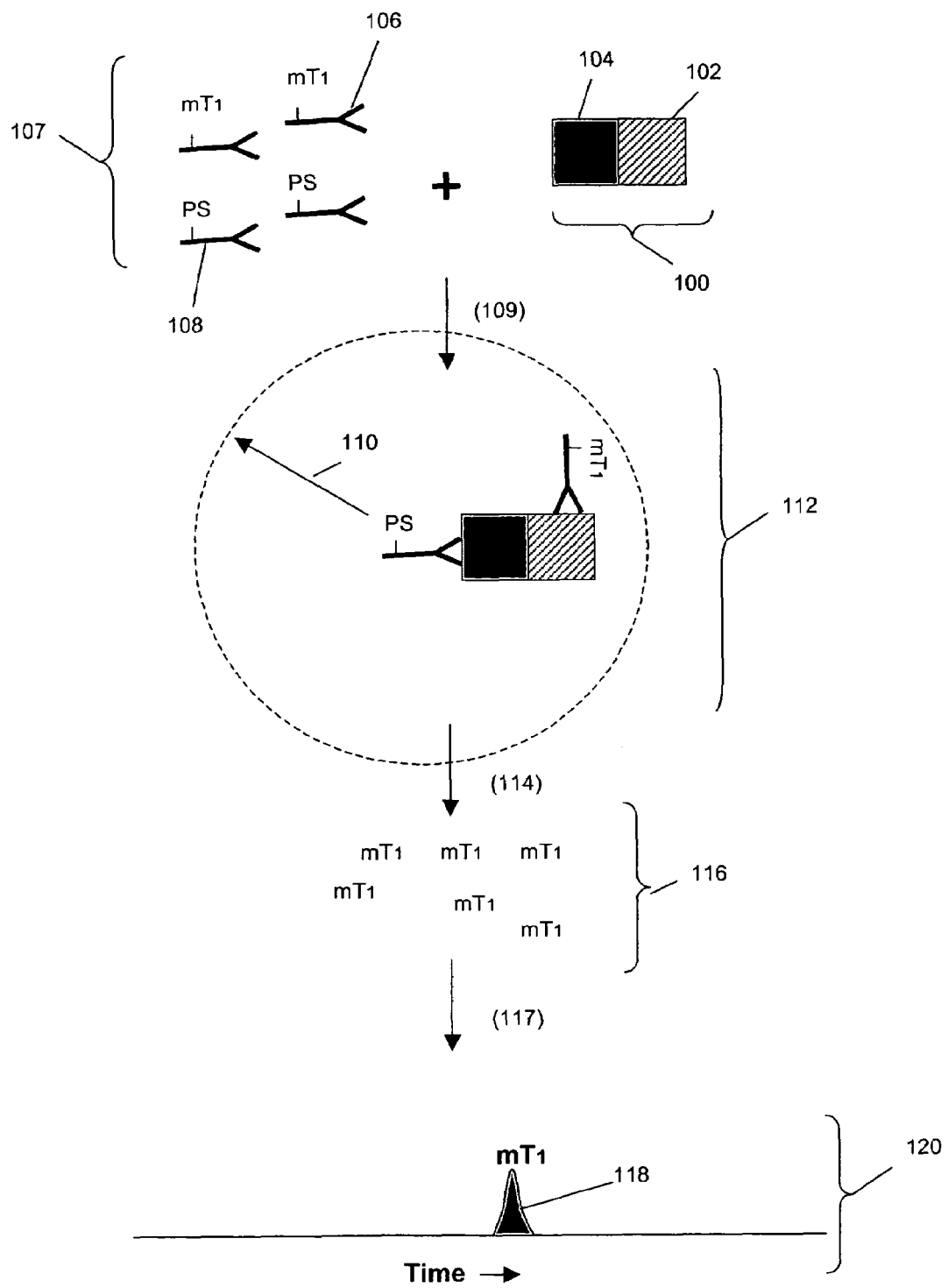
FIGS. 1A-1F illustrate diagrammatically the use of releasable molecular tags to measure various protein-protein complexes.

"Antibody" means an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular polypeptide is maintained.

"Antibody binding composition" means a molecule or a complex of molecules that comprises one or more antibodies, or fragments thereof, and derives its binding specificity from such antibody or antibody fragment. Antibody binding compositions include, but are not limited to, (i) antibody pairs in which a first antibody binds specifically to a target molecule and a second antibody binds specifically to a constant region of the first antibody; a biotinylated antibody that binds specifically to a target molecule and a streptavidin protein, which protein is derivatized with moieties such as molecular tags or photosensitizers, or the like, via a biotin moiety; (ii) antibodies specific for a target molecule and conjugated to a polymer, such as dextran, which, in turn, is derivatized with moieties such as molecular tags or photosensitizers, either directly by covalent bonds or indirectly via streptavidin-biotin linkages; (iii) antibodies specific for a target molecule and conjugated to a bead, or microbead, or other solid phase support, which, in turn, is derivatized either directly or indirectly with moieties such as molecular tags or photosensitizers, or polymers containing the latter.

"Antigenic determinant," "determinant," or "epitope" means a site on the surface of a molecule, usually a protein, to which a single antibody molecule binds; generally a protein has several or many different antigenic determinants and reacts with antibodies of many different specificities. A preferred antigenic determinant is a phosphorylation site of a protein.

"Binding moiety" means any molecule to which molecular tags can be directly or indirectly attached that is capable of specifically binding to an analyte. Binding moieties include, but are not limited to, antibodies, antibody binding compositions, peptides, proteins, nucleic acids, and organic molecules having a molecular weight of up to 1000 daltons and consisting of atoms selected from the group consisting of hydrogen, carbon, oxygen, nitrogen, sulfur, and phosphorus. Preferably, binding moieties are antibodies or antibody binding compositions.

"Chromatography" or "chromatographic separation" as used herein means or refers to a method of analysis in which the flow of a mobile phase, usually a liquid, containing a mixture of compounds, e.g. molecular tags, promotes the separation of such compounds based on one or more physical or chemical properties by a differential distribution between the mobile phase and a stationary phase, usually a solid. The one or more physical characteristics that form the basis for chromatographic separation of analytes, such as molecular tags, include but are not limited to molecular weight, shape, solubility, pKa, hydrophobicity, charge, polarity, and the like. In one aspect, as used herein, "high pressure (or performance) liquid chromatography" ("HPLC") refers to a liquid phase chromatographic separation that (i) employs a rigid cylindrical separation column having a length of up to 300 mm and an inside diameter of up to 5 mm, (ii) has a solid phase comprising rigid spherical particles (e.g. silica, alumina, or the like) having the same diameter of up to 5 μm packed into the separation column, (iii) takes place at a temperature in the range of from 35° C. to 80° C. and at column pressure up to 150 bars, and (iv) employs a flow rate in the range of from 1 μL/min to 4 mL/min. Preferably, solid phase particles for use in HPLC are further characterized in (i) having a narrow size distribution about the mean particle diameter, with substantially all particle diameters being within 10% of the mean, (ii) having the same pore size in the range of from 70 to 300 angstroms, (iii) having a surface area in the range of from 50 to 250 $m^2$/g, and (iv) having a bonding phase density (i.e. the number of retention ligands per unit area) in the range of from 1 to 5 per $nm^2$. Exemplary reversed phase chromatography media for separating molecular tags include particles, e.g. silica or alumina, having bonded to their surfaces retention ligands, such as phenyl groups, cyano groups, or aliphatic groups selected from the group including $C_8$ through $C_{18}$. Chromatography in reference to the invention includes "capillary electrochromatography" ("CEC"), and related techniques. CEC is a liquid phase chromatographic technique in which fluid is driven by electroosmotic flow through a capillary-sized column, e.g. with inside diameters in the range of from 30 to 100 μm. CEC is disclosed in Svec, Adv. Biochem. Eng. Biotechnol. 76: 1-47 (2002); Vanhoenacker et al, Electrophoresis, 22: 4064-4103 (2001); and like references. CEC column may use the same solid phase materials as used in conventional reverse phase HPLC and additionally may use so-called "monolithic" non-particular packings. In some forms of CEC, pressure as well as electroosmosis drives an analyte-containing solvent through a column.

"Complex" as used herein means an assemblage or aggregate of molecules in direct or indirect contact with one another. As used herein, "contact," or more particularly, "direct contact" in reference to a complex of molecules, or in reference to specificity or specific binding, means two molecules are close enough that weak noncovalent chemical interactions, such as Van der Waal forces, hydrogen bonding, ionic and hydrophobic interactions, and the like, dominate the interaction of the molecules. Generally, a complex of molecules is stable in that under assay conditions the complex is thermodynamically more favorable than a non-aggregated state of its component molecules. As used herein, "complex" usually refers to a stable aggregate of two or more proteins, and is equivalently referred to as a "protein-protein complex." As used herein, an "intracellular complex" or "intracellular protein-protein complex," refers to a complex of proteins normally found in the cytoplasm or nucleus of a biological cell. In one aspect, a complex is a stable aggregate comprising two proteins, or from 2 to 4 proteins, or from 2 to 6 proteins. As used herein, a "signaling complex" is an intracellular protein-protein complex that is a component of a signaling pathway.

The term "early stage cancer" as used herein refers to those cancers which have been clinically determined to be organ-confined. Also included are tumors too small to be detected by conventional methods such as mammography for breast cancer patients, or X-rays for lung cancer patients. While mammography can detect tumors having approximately $2\times10^8$ cells, the methods of the present invention should enable detection of circulating cancer cells from tumors approximating this size or smaller.

The term "enrichment" as used herein refers to the enrichment of mononuclear cells from a biological sample. In cases where peripheral blood is used as the starting materials, red cells are not counted when assessing the extent of enrichment. Using the method of the present invention, circulating epithelial cells may be enriched relative to leucocytes to the extent of at least 2,500 fold, more preferably 5,000 fold and most preferably 10,000 fold.

"ErbB receptor" means a human receptor protein of the set including Her1 (also referred to as epidermal growth factor receptor, or EGFR, or ErbB1), Her2 (also referred to as ErbB2), Her3 (also referred to as ErbB3), Her4 (also referred to as ErbB4), and proteins having substantially identical amino acid sequences thereof. Her1, Her2, Her3, and Her4 are described under NCBI accession numbers NP_005219; NP_004439 or P04626; NP_001973; and NP_005226; respectively.

The term "isolated" in reference to a polypeptide or protein means substantially separated from the components of its natural environment. Preferably, an isolated polypeptide or protein is a composition that consists of at least eighty percent of the polypeptide or protein identified by sequence on a weight basis as compared to components of its natural environment; more preferably, such composition consists of at least ninety-five percent of the polypeptide or protein identified by sequence on a weight basis as compared to components of its natural environment; and still more preferably, such composition consists of at least ninety-nine percent of the polypeptide or protein identified by sequence on a weight basis as compared to components of its natural environment. Most preferably, an isolated polypeptide or protein is a homogeneous composition that can be resolved as a single spot after conventional separation by two-dimensional gel electrophoresis based on molecular weight and isoelectric point. Protocols for such analysis by conventional two-dimensional gel electrophoresis are well known to one of ordinary skill in the art, e.g. Hames and Rickwood, Editors, Gel Electrophoresis of Proteins: A Practical Approach (IRL Press, Oxford, 1981); Scopes, Protein Purification (Springer-Verlag, New York, 1982); Rabilloud, Editor, Proteome Research: Two-Dimensional Gel Electrophoresis and Identification Methods (Springer-Verlag, Berlin, 2000).

As used herein, the term "kit" refers to any delivery system for delivering materials. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

The term "percent identical," or like term, used in respect of the comparison of a reference sequence and another sequence (i.e. a "candidate" sequence, means that in an optimal alignment between the two sequences, the candidate sequence is identical to the reference sequence in a number of subunit positions equivalent to the indicated percentage, the subunits being nucleotides for polynucleotide comparisons or amino acids for polypeptide comparisons. As used herein, an "optimal alignment" of sequences being compared is one that maximizes matches between subunits and minimizes the number of gaps employed in constructing an alignment. Percent identities may be determined with commercially available implementations of algorithms described by Needleman and Wunsch, J. Mol. Biol., 48: 443-453 (1970)("GAP" program of Wisconsin Sequence Analysis Package, Genetics Computer Group, Madison, Wis.). Other software packages in the art for constructing alignments and calculating percentage identity or other measures of similarity include the "Best-Fit" program, based on the algorithm of Smith and Waterman, Advances in Applied Mathematics, 2: 482-489 (1981) (Wisconsin Sequence Analysis Package, Genetics Computer Group, Madison, Wis.). In other words, for example, to obtain a polypeptide having an amino acid sequence at least 95 percent identical to a reference amino acid sequence, up to five percent of the amino acid residues in the reference sequence many be deleted or substituted with another amino acid, or a number of amino acids up to five percent of the total amino acid residues in the reference sequence may be inserted into the reference sequence. These alterations of the reference sequence many occur at the amino or carboxy terminal positions of the reference amino acid sequence or anywhere between those terminal positions, interspersed either individually among residues in the reference sequence of in one or more contiguous groups with in the references sequence. It is understood that in making comparisons with reference sequences of the invention that candidate sequence may be a component or segment of a larger polypeptide or polynucleotide and that such comparisons for the purpose computing percentage identity is to be carried out with respect to the relevant component or segment.

"Polypeptide" refers to a class of compounds composed of amino acid residues chemically bonded together by amide linkages with elimination of water between the carboxy group of one amino acid and the amino group of another amino acid. A polypeptide is a polymer of amino acid residues, which may contain a large number of such residues. Peptides are similar to polypeptides, except that, generally, they are comprised of a lesser number of amino acids. Peptides are sometimes referred to as oligopeptides. There is no clear-cut distinction between polypeptides and peptides. For convenience, in this disclosure and claims, the term "polypeptide" will be used to refer generally to peptides and polypeptides. The amino acid residues may be natural or synthetic.

"Protein" refers to a polypeptide, usually synthesized by a biological cell, folded into a defined three-dimensional structure. Proteins are generally from about 5,000 to about 5,000,000 or more in molecular weight, more usually from about 5,000 to about 1,000,000 molecular weight, and may include posttranslational modifications, such acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, farnesylation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, phosphorylation, prenylation, racemization, selenoylation, sulfation, and ubiquitination, e.g. Wold, F., Post-translational Protein Modifications: Perspectives and Prospects, pgs. 1-12 in Post-translational Covalent Modification of Proteins, B. C. Johnson, Ed., Academic Press, New York, 1983. Proteins include, by way of illustration and not limitation, cytokines or interleukins, enzymes such as, e.g., kinases, proteases, galactosidases and so forth, protamines, histones, albumins, immunoglobulins, scleroproteins, phosphoproteins, mucoproteins, chromoproteins, lipoproteins, nucleoproteins, glycoproteins, T-cell receptors, proteoglycans, and the like.

"Receptor tyrosine kinase," or "RTK," means a human receptor protein having intracellular kinase activity and being selected from the set of proteins listed in Table II and proteins having amino acid sequences substantially identical thereto. RTKs are described in Schlessinger, Cell, 103: 211-225 (2000); and Blume-Jensen and Hunter (cited above). "Receptor tyrosine kinase dimer" means a complex in a cell surface membrane comprising two receptor tyrosine kinase proteins. In some aspects, a receptor tyrosine kinase dimer may comprise two covalently linked receptor tyrosine kinase proteins.

The term "sample" means a quantity of material that is suspected of containing one or more molecular complexes that are to be detected or measured. As used herein, the term includes a specimen (e.g., a biopsy or medical specimen, also referred to as a "patient sample") or a culture (e.g., microbiological culture). It also includes both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. In particular, biological samples include fixed biological specimens, such as patient biopsy specimens treated with a fixative, biological specimens embedded in paraffin, frozen biological specimens, smears, and the like.

A "separation profile" in reference to the separation of molecular tags means a chart, graph, curve, bar graph, or other representation of signal intensity data versus a parameter related to the molecular tags, such as retention time, mass, or the like, that provides a readout, or measure, of the number of molecular tags of each type produced in an assay. A separation profile may be an electropherogram, a chromatogram, an electrochromatogram, a mass spectrogram, or like graphical representation of data depending on the separation technique employed. A "peak" or a "band" or a "zone" in reference to a separation profile means a region where a separated compound is concentrated. There may be multiple separation profiles for a single assay if, for example, different molecular tags have different fluorescent labels having distinct emission spectra and data is collected and recorded at multiple wavelengths. In one aspect, released molecular tags are separated by differences in electrophoretic mobility to form an electropherogram wherein different molecular tags correspond to distinct peaks on the electropherogram. A measure of the distinctness, or lack of overlap, of adjacent peaks in an electropherogram is "electrophoretic resolution," which may be taken as the distance between adjacent peak maximums divided by four times the larger of the two standard deviations of the peaks. Preferably, adjacent peaks have a resolution of at least 1.0, and more preferably, at least 1.5, and most preferably, at least 2.0. In a given separation and detection system, the desired resolution may be obtained by selecting a plurality of molecular tags whose members have electrophoretic mobilities that differ by at least a peak-resolving amount, such quantity depending on several factors well known to those of ordinary skill, including signal detection system, nature of the fluorescent moieties, the diffusion coefficients of the tags, the presence or absence of sieving matrices, nature of the electrophoretic apparatus, e.g. presence or absence of channels, length of separation channels, and the like. Electropherograms may be analyzed to associate features in the data with the presence, absence, or quantities of molecular tags using analysis programs, such as disclosed in Williams et al, U.S. patent publication 2003/0170734 A1.

"Specific" or "specificity" in reference to the binding of one molecule to another molecule, such as a binding compound, or probe, for a target analyte or complex, means the recognition, contact, and formation of a stable complex between the probe and target, together with substantially less recognition, contact, or complex formation of the probe with other molecules. In one aspect, "specific" in reference to the binding of a first molecule to a second molecule means that to the extent the first molecule recognizes and forms a complex with another molecules in a reaction or sample, it forms the largest number of the complexes with the second molecule. In one aspect, this largest number is at least fifty percent of all such complexes form by the first molecule. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like.

As used herein, the term "spectrally resolvable" in reference to a plurality of fluorescent labels means that the fluorescent emission bands of the labels are sufficiently distinct, i.e. sufficiently non-overlapping, that molecular tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558; 4,811,218, or the like, or in Wheeless et al, pgs. 21-76, in Flow Cytometry: Instrumentation and Data Analysis (Academic Press, New York, 1985).

"Substantially identical" in reference to proteins or amino acid sequences of proteins in a family of related proteins that are being compared means either that one protein has an amino acid sequence that is at least fifty percent identical to the other protein or that one protein is an isoform or splice variant of the same gene as the other protein. In one aspect, substantially identical means one protein, or amino acid sequence thereof, is at least eighty percent identical to the other protein, or amino acid sequence thereof.

DETAILED DESCRIPTION OF THE INVENTION

The invention is directed to methods and kits for detecting rare cell types in a biological specimen, such as a blood sample. Rare cell types may include many different types of cells, including cancer cells, fetal cells, cells of infectious microorganisms, and the like. In an important aspect, rare cells detected by the method of the invention are cancer cells, particularly metastisized cancer cells circulating in a patient's blood stream.

In one aspect, rare circulating cells are captured via a capture antigen that is attached to a magnetic particle for separation. Capture antigens may be any cell surface antigen that is differentially expressed on the target cells. Preferably, capture antigens are cell surface receptors that are expressed exclusively on the target cells, or that are over expressed on the target cells relative to other cells in circulation. Magnetic particles are provided that have attached an antibody composition specific for such capture antigen. These magnetic particles are mixed with a blood sample suspected of containing the rare target cell types under conditions that allow the antibody composition for form a stable complex with capture antigens whenever present in the sample. A magnetic field is then applied to the magnetic particles to immobilize them during a washing step to remove un-complexed material, or transport captured cells away from the un-complexed material. In either case, a population of cells is formed that is enriched for those having the capture antigen. The enriched population is then assayed for the presence of one or more biomarkers using binding compounds with releasable molecular tags. In one aspect, cells of the enriched population are lysed and then the lysate is combined with binding compounds specific for predetermined biomarkers. After stable complexes are formed between the biomarkers and the binding compounds, the molecular tags are released from the binding compounds in the complexes. In some embodiments, binding compounds failing to form stable complexes are removed, e.g. in a wash step, after which molecular tags are released from the binding compounds forming stable complexes. In such embodiments (i.e. heterogeneous formats), as explained below, a wide range of cleavable linkages are available. In other embodiments, no wash step is preformed because a cleaving agent is employed that acts locally to a complex. After cleavage, the molecular tags are then separated and detected. The presence or absence and/or quantity of each molecular tag gives information on the presence, quantity, and types of circulating target cells.

Preferably, circulating target cells are metastatic cancer cells, and such cells are enriched using antibodies specific for conventional capture antigens.

In one aspect, the invention includes the use of intracellular complexes as biomarkers for disease or other physiological conditions. For example, a plurality of intracellular complexes as well as conventional biomarkers, such as individual proteins, are simultaneously measured in the same assay reaction mixture. Preferably, such complexes are measured using binding compounds having one or more molecular tags releasably attached, such that after binding to a protein in a complex, the molecular tags may be released and separated from the reaction, or assay, mixture, as described above.

In one such embodiment, the invention provides a method for determining a disease status of a patient comprising the following steps: (i) immunomagnetically isolating from a patient sample a subpopulation of cells containing a rare cell type by contacting the sample with one or more antibody compositions, each antibody composition being specific for a capture antigen and being attached to a magnetic particle; (ii) measuring an amount of each of one or more intracellular protein-protein complexes in the subpopulation; comparing each such amount to its corresponding amount from a reference sample; and correlating differences in the amounts from the subpopulation and the respective corresponding amounts from the reference sample to the presence or severity of a disease condition in the patient. In a preferred embodiment, the step of measuring comprising the steps of: (i) providing one or more binding compounds specific for a protein of each of the one or more complexes, such that each binding compound has one or more molecular tags each attached thereto by a cleavable linkage, and such that the one or more molecular tags attached to different binding compounds have different separation characteristics so that upon separation molecular tags from different binding compounds form distinct peaks in a separation profile; (ii) mixing the binding compounds and the one or more complexes such that binding compounds specifically bind to their respective proteins of the complexes to form detectable complexes; (iii) cleaving the cleavable linkage of each binding compound forming detectable complexes, and (iv) separating and identifying the released molecular tags to determine the presence or absence or the amount of the one or more complexes of proteins.

In another aspect, the step of measuring the amounts of one or more complexes comprising the following steps: (i) providing for each of the one or more complexes a cleaving probe specific for a first protein in each of the one or more complexes, each cleaving probe having a cleavage-inducing moiety with an effective proximity; (ii) providing one or more binding compounds specific for a second protein of each of the one or more complexes, such that each binding compound has one or more molecular tags each attached thereto by a cleavable linkage, and such that the one or more molecular tags attached to different binding compounds have different separation characteristics so that upon separation molecular tags from different binding compounds form distinct peaks in a separation profile; (iii) mixing the cleaving probes, the binding compounds, and the one or more complexes such that cleaving probes specifically bind to first proteins of the complexes and binding compounds specifically bind to the second proteins of the complexes and such that cleavable linkages of the binding compounds are within the effective proximity of cleavage-inducing moieties of the cleaving probes so that molecular tags are released; and (iv) separating and identifying the released molecular tags to determine the presence or absence or the amount of the one or more complexes of proteins.

In one aspect, the invention is implemented by methods employing cleaving probes that generate a locally acting cleaving agent and binding compounds labeled with releasable molecular tags that are released by the cleaving agent. Complex formation is detected by designing cleaving probes and binding compounds such that at least one cleaving probe specifically binds to a different component of a complex than at least one of the binding compounds. In this manner, molecular tags of a predetermined type are released only when a complex is formed.

Figure 1B:
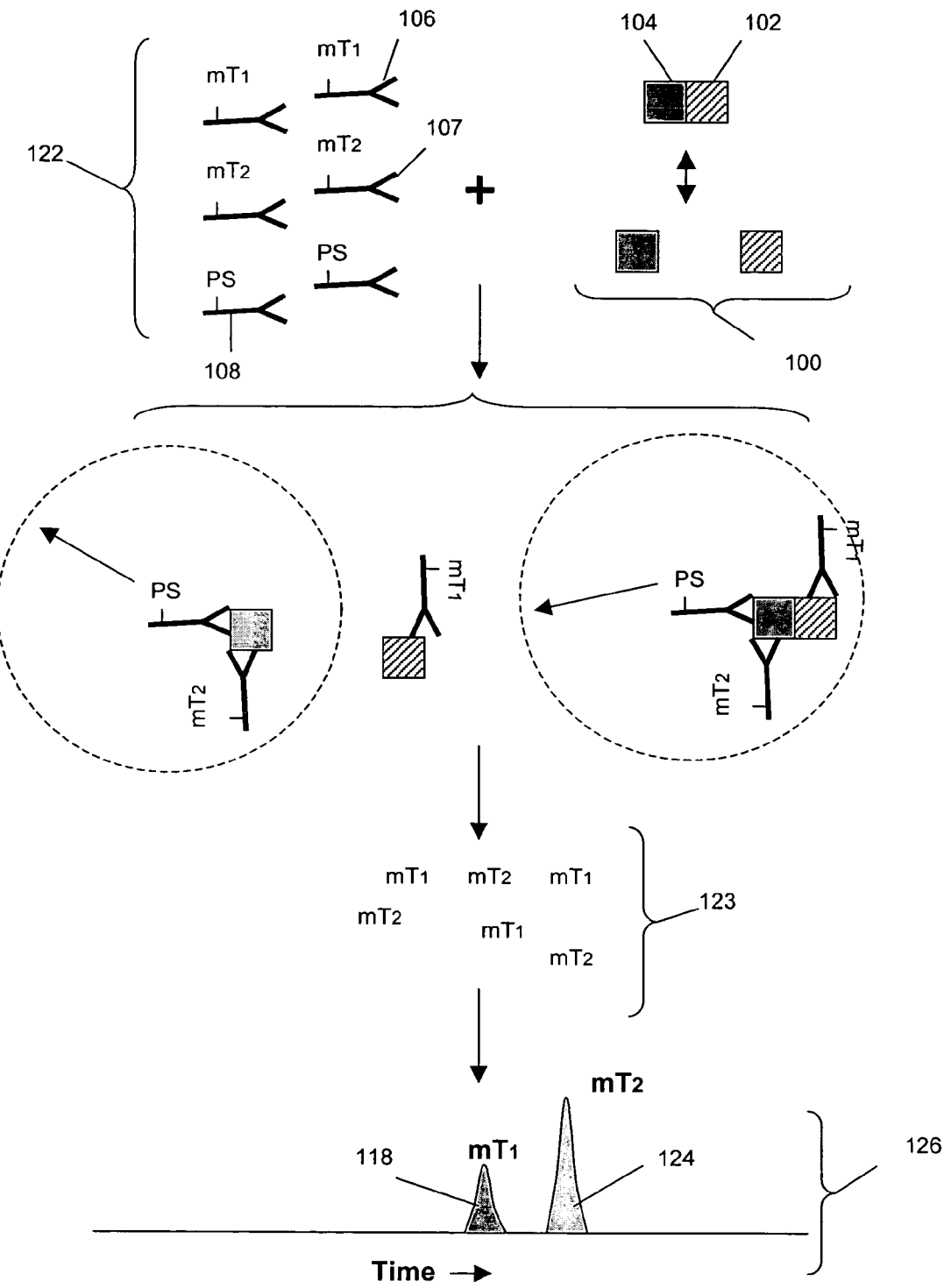
Figure 1C:
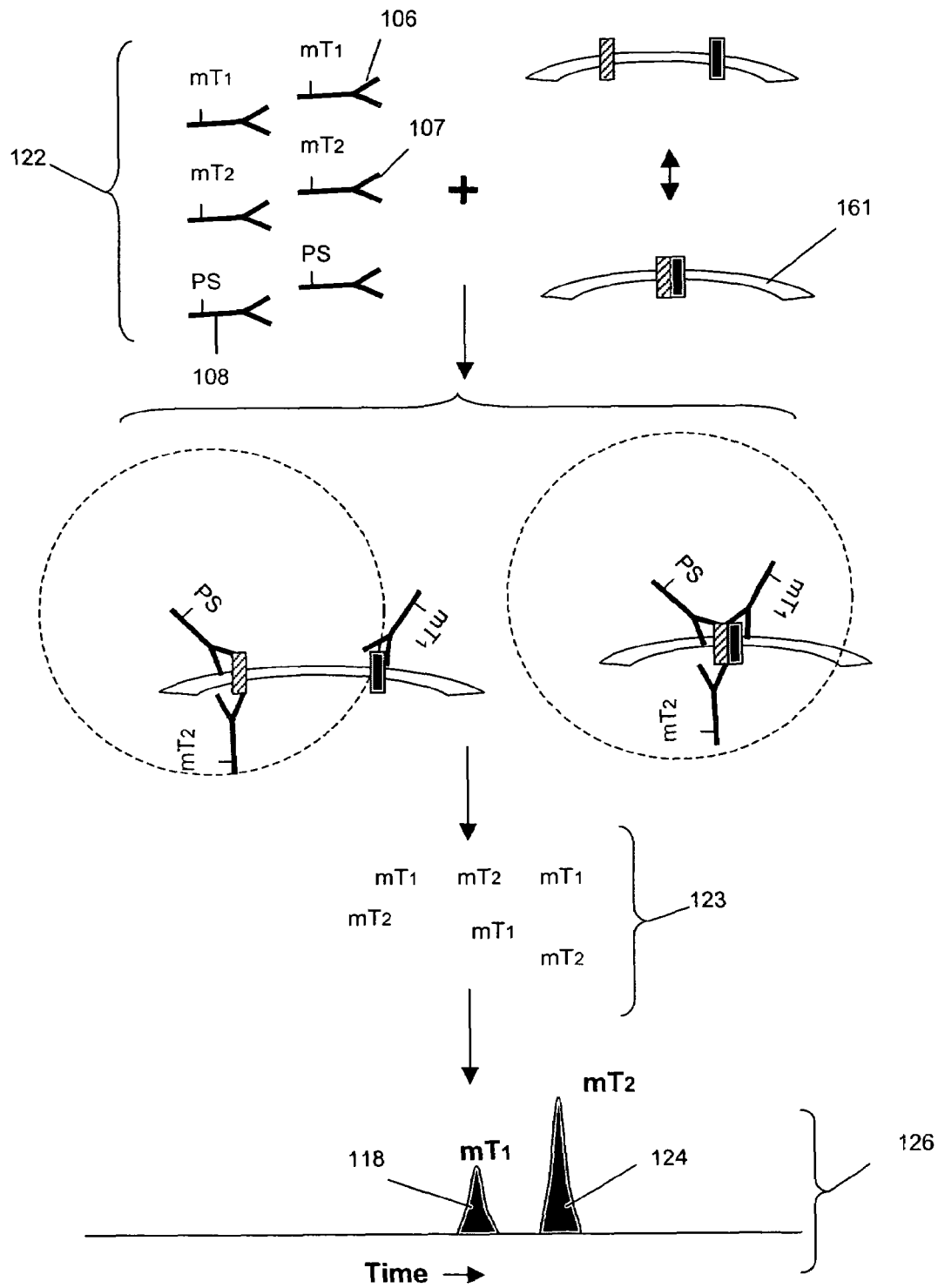

The operation of one embodiment of the invention is illustrated in FIG. 1A. Molecular complex (100) forms by the binding of proteins (104) and (102), e.g. 14-3-3 and phosphorylated BAD. Reagents (107) of the invention, comprising cleaving probes (108) (in this illustration having photosensitizer "PS" attached) and binding compounds (106), are mixed (109) with a sample containing complex (100) under conditions that permit the specific binding (112) of cleaving probes (108) and binding compounds (106) to their respective antigenic determinants on complex (100) that are on different proteins of the complex. After binding, and optionally washing or buffer exchange, cleaving probes (108) are activated to generate an active species that, e.g. in the case of singlet oxygen, diffuses out from a photosensitizers to an effective proximity (110). Cleavable linkages within this proximity are cleaved and molecular tags are released (114). Released molecular tags (116) are then separated (117) and a separation profile (120), such as an electropherogram, is produced, in which peak (118) is identified and correlated to molecular tag, "$mT_1$." By employing additional binding compounds and molecular tags, additional complexes may be measured. A more complex embodiment is illustrated in FIG. 1B, in which an additional binding compound is employed to give a measure of the total amount of protein (104) in a sample. Reagents (122) of the invention comprise (i) cleaving probes (108), first binding compound (106), and second binding compound (107), wherein first binding compound (106) is specific for protein (102) and second binding compound (107) is specific for protein (104) at a different antigenic determinant than that cleaving probe (108) is specific for. As with the embodiment of FIG. 1A, after binding of the reagents, cleaving probe (108) is activated to produce active species that cleave the cleavable linkages of the molecular tags within the effective proximity of the photosensitizer. In this embodiment, molecular tags are released from monomers of protein (104) that have both reagents (107) and (108) attached and from heterodimers that have reagent (108) attached and either or both of reagents (106) and (107) attached. Released molecular tags (123) are separated, and peaks (118 and 124) in a separation profile (126) are correlated to the amounts of the released molecular tags. In this embodiment, relative peak heights, or areas, may reflect (i) the differences in affinity of the first and second binding compounds for their respective antigenic determinants, and/or (ii) the presence or absense of the antigenic determinant that the binding compound is specific for. The later situation is important whenever a binding compound is used to monitor the post-translational state of a protein, e.g. phosphorylation state. FIG. 1C illustrates that complexes detected by the invention include receptor dimers and oligomer, e.g. anchored in membrane (161).

Figure 1D:
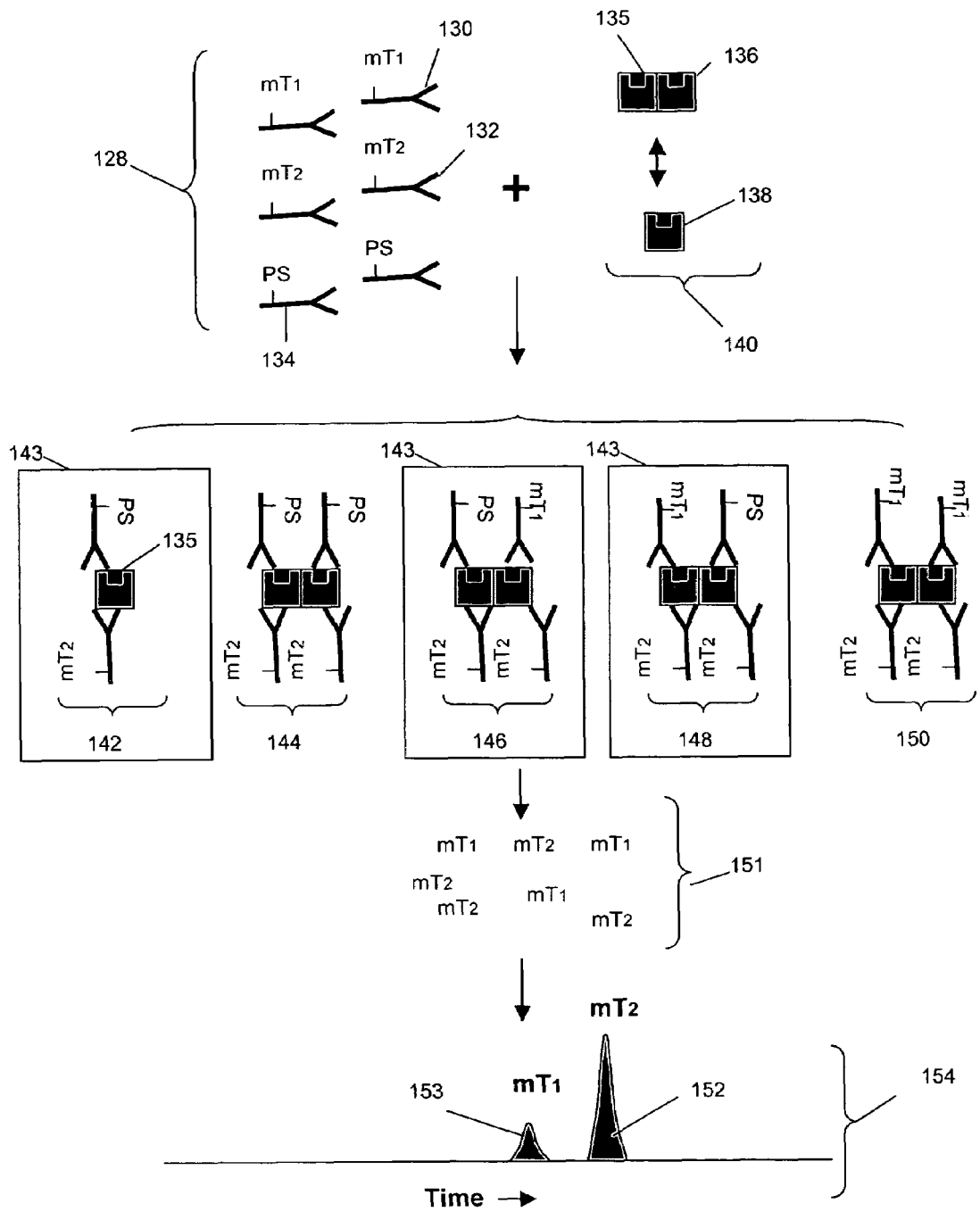

FIG. 1D illustrates one approach for measuring homodimeric complexes. As above, an assay may comprise three reagents (128): cleaving probes (134), first binding compound (130), and second binding compound (132). First binding compound (130) and cleaving probe (134) are constructed to be specific for the same antigenic determinant (135) on protein (138) that exists (140) in a sample as either a homodimer (136) or a monomer (138). After reagents (128) are combined with a sample under conditions that promote the formation of stable complexes between the reagents and their respective targets, multiple complexes (142 through 150) form in the assay mixture. Because cleaving probe (134) and binding compound (130) are specific for the same antigenic determinant (135), four different combinations (144 throught 150) of reagents may form complexes with homodimers. Of the complexes in the assay mixture, only those (143) with both a cleaving probe (134) and at least one binding compound will contribute released molecular tags (151) for separation and detection (154). In this embodiment, the size of peak (153) is proportional to the amount of homodimer in the assay mixture, while the size of peak (152) is proportional to the total amount of protein (138) in the assay mixture, both in monomeric form (142) or in homodimeric form (146 and 148).

Figure 1E:
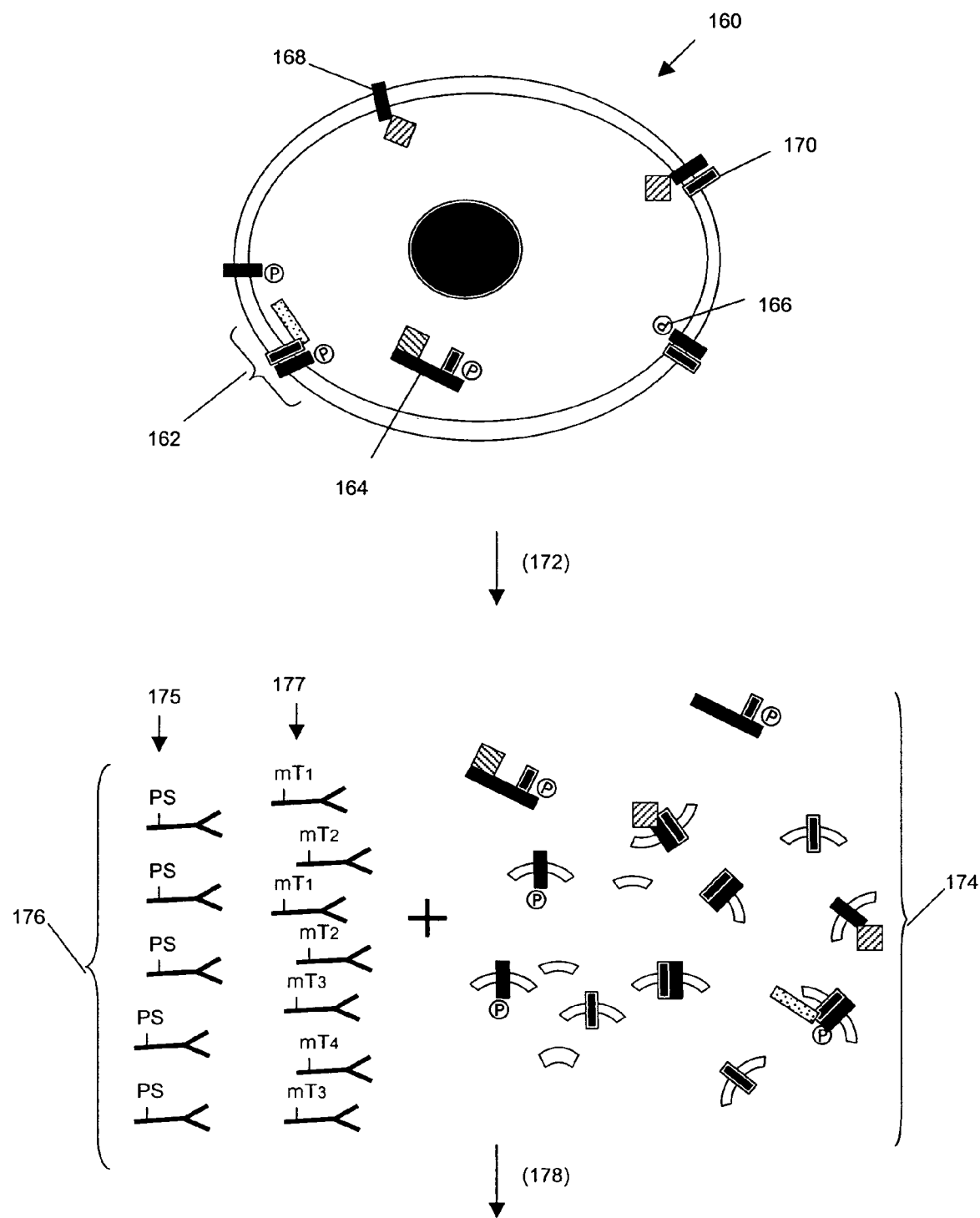
Figure 1F:
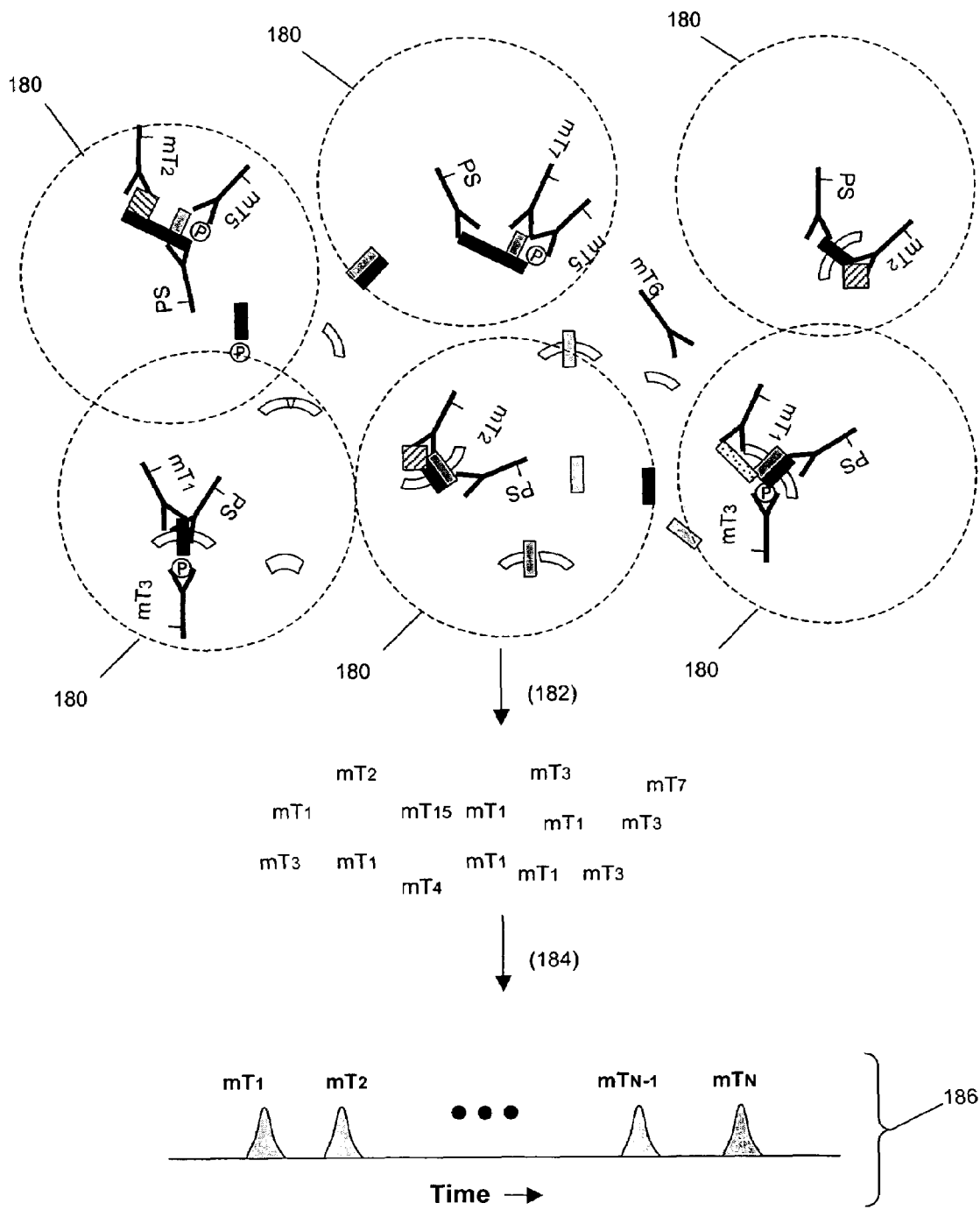

Another aspect of the invention is illustrated in FIGS. 1E and 1F, which provides for the simultaneous detection or measurement of multiple complexes in a cellular sample. Cells (160), which may be from a sample from in vitro cultures or from a specimen of patient tissue, are lysed (172) to render accessible molecular complexes associated with the cell membrane, and/or within the cytosol, and/or within the cell nucleus. Complexes associated with apoptotic signaling include, but are not limited to, surface receptor complexes, such as receptor dimers, receptor complexes including adaptor or scaffold molecules of various types, dimers and higher order complexes of intracellular proteins, phosphorylation sites of proteins in such complexes, and the like. After lysing, the resulting lysate (174) is combined with assay reagents (176) that include multiple cleaving probes (175) and multiple binding compounds (177). Assay conditions are selected (178) that allow reagents (176) to specifically bind to their respective targets, so that upon activation cleavable linkages within the effective proximity (180) of the cleavage-inducing moieties are cleaved and molecular tags are released (182). As above, after cleavage, the released molecular tags are separated (184) and identified in a separation profile (186), such as an electropherogram, and based on the number and quantities of molecular tags measured, a profile is obtained of the selected molecular complexes in the cells of the sample.

As described more fully below, biomarker of rare cells are determined by separation and identification of the released molecular tags. A wide variety of separation techniques may be employed that can distinguish molecules based on one or more physical, chemical, or optical differences among molecules being separated including but not limited to electrophoretic mobility, molecular weight, shape, solubility, pKa, hydrophobicity, charge, charge/mass ratio, polarity, or the like. In one aspect, molecular tags in a plurality differ in electrophoretic mobility and optical detection characteristics and are separated by electrophoresis. In another aspect, molecular tags in a plurality differ in molecular weight, shape, solubility, pKa, hydrophobicity, charge, polarity, and are separated by normal phase or reverse phase HPLC, ion exchange HPLC, capillary electrochromatography, mass spectroscopy, gas phase chromatography, or like technique.

Sets of molecular tags may be provided that are separated into distinct bands or peaks by a separation technique after they are released from binding compounds. Molecular tags within a set may be chemically diverse; however, for convenience, sets of molecular tags are usually chemically related. For example, they may all be peptides, or they may consist of different combinations of the same basic building blocks or monomers, or they may be synthesized using the same basic scaffold with different substituent groups for imparting different separation characteristics, as described more fully below. The number of molecular tags in a plurality may vary depending on several factors including the mode of separation employed, the labels used on the molecular tags for detection, the sensitivity of the binding moieties, the efficiency with which the cleavable linkages are cleaved, and the like. In one aspect, the number of molecular tags in a plurality ranges from 2 to several tens, e.g. 30. In other aspects, the size of the plurality may be in the range of from 2 to 20, 2 to 10, 3 to 20, 3 to 10, 4 to 30, 4 to 10, 5 to 20, or 5 to 10.

Isolation of Target Cells

In one aspect, a population of cells enriched for rare cells of interest is isolated from a specimen. Biomarkers are then detected and/or quantified in a sample of the population using binding compounds with releasable molecular tags. Preferably, the enrichment is carried out immunomagnetically with magnetic particles derivatized with antibody compositions specific for predetermined capture antigens.

A. Magnetic Isolation of Cells. Immunomagnetic isolation or enrichment may be carried out using a variety of techniques and materials known in the art, as disclosed in the following representative references that are incorporated by reference: Terstappen et al, U.S. Pat. No. 6,365,362; Terstappen et al, U.S. Pat. No. 5,646,001; Rohr et al, U.S. Pat. No. 5,998,224; Kausch et al, U.S. Pat. No. 5,665,582; Kresse et al, U.S. Pat. No. 6,048,515; Kausch et al, U.S. Pat. No. 5,508,164; Miltenyi et al, U.S. Pat. No. 5,691,208; Molday, U.S. Pat. No. 4,452,773; Kronick, U.S. Pat. No. 4,375,407; Radbruch et al, chapter 23, in Methods in Cell Biology, Vol, 42 (Academic Press, New York, 1994); Uhlen et al, Advances in Biomagnetic Separation (Eaton Publishing, Natick, 1994); Safarik et al, J. Chromatography B, 722: 33-53 (1999); Miltenyi et al, Cytometry, 11: 231-238 (1990); Nakamura et al, Biotechnol. Prog., 17: 1145-1155 (2001); Moreno et al, Urology, 58: 386-392 (2001); Racila et al, Proc. Natl. Acad. Sci., 95: 4589-4594 (1998); Zigeuner et al, J. Urology, 169: 701-705 (2003); Ghossein et al, Seminars in Surgical Oncology, 20: 304-311 (2001).

The preferred magnetic particles for use in carrying out this invention are particles that behave as colloids. Such particles are characterized by their sub-micron particle size, which is generally less than about 200 nanometers (nm) (0.20 microns), and their stability to gravitational separation from solution for extended periods of time. In addition to the many other advantages, this size range makes them essentially invisible to analytical techniques commonly applied to cell analysis. Particles within the range of 90-150 nm and having between 70-90% magnetic mass are contemplated for use in the present invention. Suitable magnetic particles are composed of a crystalline core of superparamagnetic material surrounded by molecules which are bonded, e.g., physically absorbed or covalently attached, to the magnetic core and which confer stabilizing colloidal properties. The coating material should preferably be applied in an amount effective to prevent non specific interactions between biological macromolecules found in the sample and the magnetic cores. Such biological macromolecules may include sialic acid residues on the surface of non-target cells, lectins, glyproteins and other membrane components. In addition, the material should contain as much magnetic mass/nanoparticle as possible. The size of the magnetic crystals comprising the core is sufficiently small that they do not contain a complete magnetic domain. The size of the nanoparticles is sufficiently small such that their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Finally, the magnetic particles should be separable in high magnetic gradient external field separators. That characteristic facilitates sample handling and provides economic advantages over the more complicated internal gradient columns loaded with ferromagnetic beads or steel wool. Magnetic particles having the above-described properties can be prepared by modification of base materials described in U.S. Pat. Nos. 4,795,698, 5,597,531 and 5,698,271, which patents are incorporated by reference.

B. Sample Preparation. Samples are prepared for assays of the invention using conventional techniques, which may depend on the source from which a sample is taken. Guidance for sample preparation techniques can be found in standard treatises, such as Sambrook et al, Molecular Cloning, Second Edition (Cold Spring Harbor Laboratory Press, New York, 1989); Innis et al, editors, PCR Protocols (Academic Press, New York, 1990); Berger and Kimmel, "Guide to Molecular Cloning Techniques," Vol. 152, Methods in Enzymology (Academic Press, New York, 1987); Ohlendieck, K. (1996). Protein Purification Protocols; Methods in Molecular Biology, Humana Press Inc., Totowa, N.J. Vol 59: 293-304; Method Booklet 5, "Signal Transduction" (Biosource International, Camarillo, Calif., 2002); or the like.

For blood specimens, the following references provide guidance for separating red blood cells from other cells in a specimen and for combining such other cells with immunomagnetic particles: Nakamura et al, Biotechnol. Prog., 17: 1145-1155 (2001); Moreno et al, Urology, 58: 386-392 (2001); Racila et al, Proc. Natl. Acad. Sci., 95: 4589-4594 (1998); Zigeuner et al, J. Urology, 169: 701-705 (2003); Ghossein et al, Seminars in Surgical Oncology, 20: 304-311 (2001); Terstappen et al, U.S. Pat. No. 6,365,362.

In some embodiments, after immunomagnetic isolation of desired cells, lysates may be prepared by conventional cell lysis techniques (e.g. 0.14 M NaCl, 1.5 mM $MgCl_2$, 10 mM Tris-Cl (pH 8.6), 0.5% Nonidet P-40, and protease and/or phosphatase inhibitors as required).

C. Exemplary Blood Sample Collection and Immunomagnetic Enrichment. The following procedure may be used to obtain a sample of cells from a patient's blood in order to detect or quantify biomarkers of cancer cells from epithelial tumors. 8-20 ml blood samples are obtained from controls and patients, e.g. with carcinoma of the breast, prostate and/or colon. The blood samples are drawn into Vacutainer tubes (Becton-Dickinson) containing EDTA as anticoagulant. The samples are kept at room temperature and processed within 24 hours after collection. Circulating epithelial cells may be enumerated in peripheral blood samples from cancer patients and in normal controls with no evidence of malignant disease. Monoclonal antibodies specific for epithelial cell adhesion molecule (EpCAM) are broadly reactive with tissue of epithelial cell origin (Stahel R A, et al. Int J Cancer Suppl. 8:6-26 (1994); Momburg F, et al. Cancer research. 47:2883-2891 (1987); Gaffey M J, et al. Am J Surg Path. 16:593-599 (1992)). The GA73.3 or MJ37 EpCAM antibodies recognizing different epitopes on EpCAM (Herlyn D, et al. J Immunol Methods. 73:157-167 (1984)) Wistar Institute, Philadelphia, Pa. and M J Mattes (De Leij L, et al. Int J Cancer Suppl. 8:60-63 (1993), or like antibodies are coupled to magnetic nanoparticles (ferrofluids) (Liberti P A & Piccoli S P, U.S. Pat. No. 5,512,332 (1996), Immunicon, Huntingdon Valley, Pa.). Blood is incubated with the anti-EpCAM conjugated ferrofluid for 15 minutes in disposable tubes with an internal diameter of 13 mm. The tubes are placed into a separator composed of four opposing magnets for 10 minutes (QMS13, Immunicon, Huntingdon Valley, Pa.). After separation, the blood is aspirated and discarded. The tube is taken out of the magnetic separator and the collected fraction is resuspended from the walls of the vessel.

Assay Components for Enriched Cell Populations

Biomarkers may be detected in assays having homogeneous formats or a non-homogeneous, i.e. heterogeneous, formats. In a homogeneous format, no step is required to separate binding compounds specifically bound to target complexes from unbound binding compounds. In a preferred embodiment, homogeneous formats employ reagent pairs comprising (i) one or more binding compounds with releasable molecular tags and (ii) at least one cleaving probe that is capable of generating an active species that reacts with and releases molecular tags within an effective proximity of the cleaving probe.

Biomarkers may also be detected by assays employing a heterogeneous format. Heterogeneous techniques normally involve a separation step, where biomarkers having binding compounds specifically bound are separated from unbound binding compounds, and optionally, other cellular components, such as proteins, membrane fragments, and the like. Separation can be achieved in a variety of ways, each employing a reagent bound to a solid support that distinguishes between complex-bound and unbound binding compounds. The solid support may be a vessel wall, e.g., microtiter well plate well, capillary, plate, slide, beads, including magnetic beads, liposomes, or the like.

When releasable molecular tags are employed in a heterogeneous format, a releasing agent, i.e. a cleavaging agent, need not be proximity dependent, since target Biomarkers are separated from unbound binding compounds. Therefore, a larger variety of cleavage protocols can be used to release molecular tags. Cleavage may still be carried out using a sensitizer, as described below, but it may also employ various types of chemical, photochemical, or enzymatic cleavage of a variety of cleavable linking groups, such as are known in the art. As described more fully below, non-limiting examples of chemically cleavable linkages include disulfides (cleavable by reduction, typically using dithiothreitol), azo groups (cleavable with dithionate), sulfones (cleavable with basic phosphate, with or without dithiothreitol), glycols, cleavable by periodate, and esters, cleavable by hydrolysis. Photolabile linkers include, for example, azo linkages and o-nitrobenzyl ethers. In particular, disulfide bonds are preferred as cleavable linkages whenever heterogeneous formats are employed.

With detection using molecular tags in a heterogeneous format, after washing, a support may be combined with a solvent into which the molecular tags are to be released. Depending on the nature of the cleavable bond and the method of cleavage, the solvent may include any additional reagents for the cleavage. Where reagents for cleavage are not required, the solvent conveniently may be a separation buffer, e.g. an electrophoretic separation medium. For example, where the cleavable linkage is photolabile, the medium may be irradiated with light of appropriate wavelength to release the molecular tags into the buffer.

In either format, if the assay reaction conditions interfere with the separation technique employed, it may be necessary to remove, or exchange, the assay reaction buffer prior to cleavage and separation of the molecular tags. For example, in some embodiments, assay conditions include salt concentrations (e.g. required for specific binding) that degrade separation performance when molecular tags are separated on the basis of electrophoretic mobility.

Guidance for selecting cleaving agents, molecular tags, cleavable linkages, and other components for homogeneous or heterogeneous assay formats is disclosed in the following references, which are incorporated by reference: U.S. Pat. No. 6,627,400; and U.S. patent publications 2003/0013126; 2003/0170915; and 2003/0203408.

As mentioned above, an aspect of the invention includes providing mixtures of pluralities of different binding compounds, wherein each different binding compound has one or more molecular tags attached through cleavable linkages. The nature of the binding compound, cleavable linkage and molecular tag may vary widely. A binding compound may comprise an antibody binding composition, an antibody, a peptide, a peptide or non-peptide ligand for a cell surface receptor, a protein, an oligonucleotide, an oligonucleotide analog, such as a peptide nucleic acid, a lectin, or any other molecular entity that is capable of specific binding or stable complex formation with an analyte of interest, such as a complex of proteins. In one aspect, a binding compound, which can be represented by the formula below, comprises one or more molecular tags attached to a binding moiety.

$B\text{-}(L\text{-}E)_k$ wherein B is binding moiety; L is a cleavable linkage; and E is a molecular tag. In homogeneous assays, cleavable linkage, L, may be an oxidation-labile linkage, and more preferably, it is a linkage that may be cleaved by singlet oxygen. The moiety "$\text{-}(L\text{-}E)_k$" indicates that a single binding compound may have multiple molecular tags attached via cleavable linkages. In one aspect, k is an integer greater than or equal to one, but in other embodiments, k may be greater than several hundred, e.g. 100 to 500, or k is greater than several hundred to as many as several thousand, e.g. 500 to 5000. Usually each of the plurality of different types of binding compound has a different molecular tag, E. Cleavable linkages, e.g. oxidation-labile linkages, and molecular tags, E, are attached to B by way of conventional chemistries.

Preferably, B is an antibody binding composition. Such compositions are readily formed from a wide variety of commercially available antibodies, both monoclonal and polyclonal, specific for proteins of interest. In particular, antibodies specific for epidermal growth factor receptors are disclosed in the following patents, which are incorporated by references: U.S. Pat. Nos. 5,677,171; 5,772,997; 5,968,511; 5,480,968; 5,811,098. U.S. Pat. No. 5,599,681, incorporated herein by reference, discloses antibodies specific for phosphorylation sites of proteins. Commercial vendors, such as Cell Signaling Technology (Beverly, Mass.), Biosource International (Camarillo, Calif.), and Upstate (Charlottesville, Va.), also provide monoclonal and polyclonal antibodies specific for many proteins, e.g. proteins in signalling pathways, including proteins listed in the tables below.

Cleavable linkage, L, can be virtually any chemical linking group that may be cleaved under conditions that do not degrade the structure or affect detection characteristics of the released molecular tag, E. Whenever a cleaving probe is used in a homogeneous assay format, cleavable linkage, L, is cleaved by a cleavage agent generated by the cleaving probe that acts over a short distance so that only cleavable linkages in the immediate proximity of the cleaving probe are cleaved. Typically, such an agent must be activated by making a physical or chemical change to the reaction mixture so that the agent produces a short lived active species that diffuses to a cleavable linkage to effect cleavage. In a homogeneous format, the cleavage agent is preferably attached to a binding moiety, such as an antibody, that targets prior to activation the cleavage agent to a particular site in the proximity of a binding compound with releasable molecular tags. In such embodiments, a cleavage agent is referred to herein as a "cleavage-inducing moiety," which is discussed more fully below.

In a non-homogeneous format, because specifically bound binding compounds are separated from unbound binding compounds, a wider selection of cleavable linkages and cleavage agents are available for use. Cleavable linkages may not only include linkages that are labile to reaction with a locally acting reactive species, such as hydrogen peroxide, singlet oxygen, or the like, but also linkages that are labile to agents that operate throughout a reaction mixture, such as base-labile linkages, photocleavable linkages, linkages cleavable by reduction, linkages cleaved by oxidation, acid-labile linkages, peptide linkages cleavable by specific proteases, and the like. References describing many such linkages include Greene and Wuts, Protective Groups in Organic Synthesis, Second Edition (John Wiley & Sons, New York, 1991); Hermanson, Bioconjugate Techniques (Academic Press, New York, 1996); and Still et al, U.S. Pat. No. 5,565,324. Exemplary cleavable linkages are illustrated in Table I.

TABLE I

| Linking Group | Cleavage Reagent |
|---|---|
| silyl | fluoride or acid |
| A | hv |
| B | Ce(NH$_4$)$_2$(NO$_3$)$_6$ |
| —NCO$_2$— | HO$^-$, H$^+$, or LiAlH$_4$ |
| C | O$_3$, OsO$_4$/IO$_4^-$, or KMnO$_4$ |
| D | 1) O$_2$ or Br$_2$, MeOH |
|  | 2) H$_3$O$^+$ |
| —Si— | oxidation, H$^+$, Br$_2$, Cl$_2$, etc. |
| E | H$_3$O$^+$ |

TABLE I-continued

| Linking Group | Cleavage Reagent |
|---|---|
| F | H$_3$O$^+$ |
| G | F$^-$ or H$^+$ |
| H, where x is a keto, ester, amide, NO$_2$, sulfide, sulfoxide, sulfone, and related electron withdrawing groups. | base, HO$^-$ |
| I | H$_3$O$^+$ or reduction (e.g. Li/NH$_3$) |
| J | (Ph$_3$P)$_3$RhCl(H) |
| K | Li, Mg, or BuLi |
| M | Hg$^{+2}$ |
| N, where x is halogen or pseudohalogen | Zn or Mg |
| O | oxidation (e.g. Pb(OAc)$_4$ or H$_3$IO$_6$) |
| P, where X is a electron withdrawing group | base |

Illustrative cleavable linking groups and cleavage reagents (L) shows the point of attachment of the molecular tag (E).

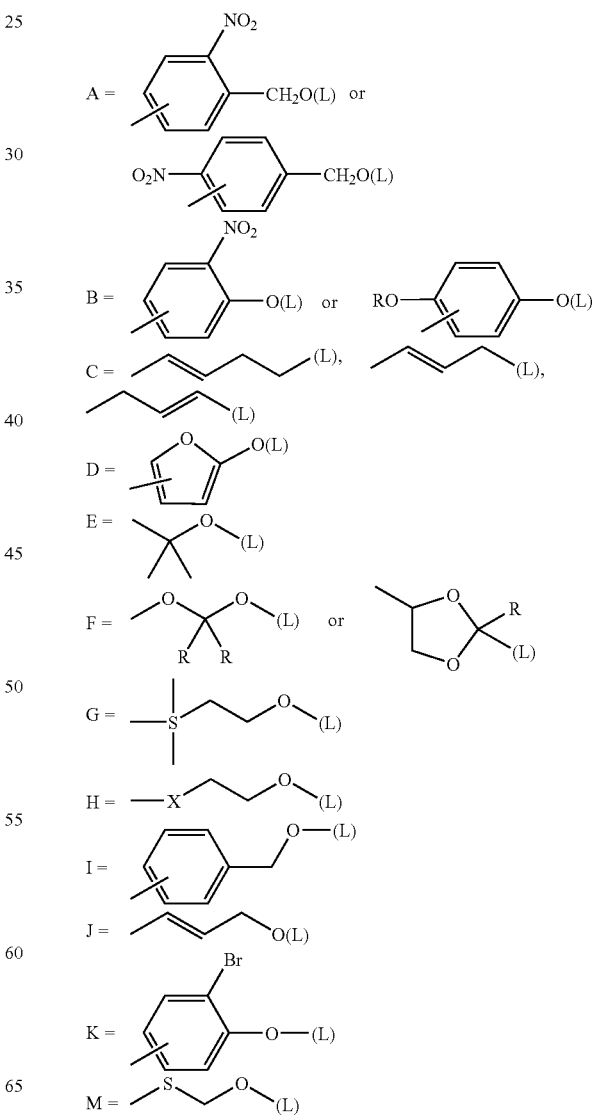

-continued

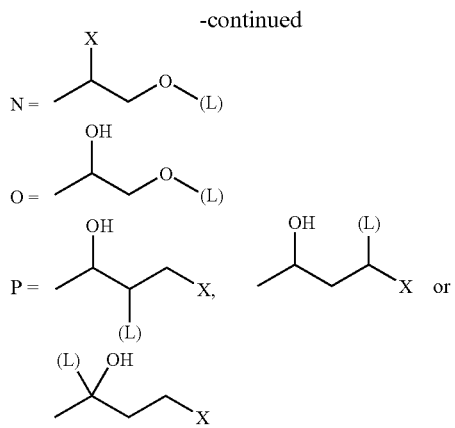

In one aspect, commercially available cleavable reagent systems may be employed with the invention. For example, a disulfide linkage may be introduced between an antibody binding composition and a molecular tag using a heterofunctional agent such as N-succinimidyl 3-(2-pyridyldithio)propionate (SPDP), succinimidyloxycarbonyl-α-methyl-α-(2-pyridyldithio)toluene (SMPT), or the like, available from vendors such as Pierce Chemical Company (Rockford, Ill.). Disulfide bonds introduced by such linkages can be broken by treatment with a reducing agent, such as dithiothreitol (DTT), dithioerythritol (DTE), 2-mercaptoethanol, sodium borohydride, or the like. Typical concentrations of reducing agents to effect cleavage of disulfide bonds are in the range of from 10 to 100 mM. An oxidatively labile linkage may be introduced between an antibody binding composition and a molecular tag using the homobifunctional NHS ester cross-linking reagent, disuccinimidyl tartarate (DST)(available from Pierce) that contains central cis-diols that are susceptible to cleavage with sodium periodate (e.g., 15 mM periodate at physiological pH for 4 hours). Linkages that contain esterified spacer components may be cleaved with strong nucleophilic agents, such as hydroxylamine, e.g. 0.1 N hydroxylamine, pH 8.5, for 3-6 hours at 37° C. Such spacers can be introduced by a homobifunctional cross-linking agent such as ethylene glycol bis(succinimidylsuccinate)(EGS) available from Pierce (Rockford, Ill.). A base labile linkage can be introduced with a sulfone group. Homobifunctional cross-linking agents that can be used to introduce sulfone groups in a cleavable linkage include bis[2-(succinimidyloxycarbonyloxy)ethyl]sulfone (BSOCOES), and 4,4-difluoro-3,3-dinitrophenylsulfone (DFDNPS). Exemplary basic conditions for cleavage include 0.1 M sodium phosphate, adjusted to pH 11.6 by addition of Tris base, containing 6 M urea, 0.1% SDS, and 2 mM DTT, with incubation at 37° C. for 2 hours. Photocleavable linkages include those disclosed in Rothschild et al, U.S. Pat. No. 5,986,076.

When L is oxidation labile, L may be a thioether or its selenium analog; or an olefin, which contains carbon-carbon double bonds, wherein cleavage of a double bond to an oxo group, releases the molecular tag, E. Illustrative thioether bonds are disclosed in Willner et al, U.S. Pat. No. 5,622,929 and in Singh et al, U.S. patent publication 2003/0013126, both of which are incorporated by reference. Illustrative olefins include vinyl sulfides, vinyl ethers, enamines, imines substituted at the carbon atoms with an α-methine (CH, a carbon atom having at least one hydrogen atom), where the vinyl group may be in a ring, the heteroatom may be in a ring, or substituted on the cyclic olefinic carbon atom, and there will be at least one and up to four heteroatoms bonded to the olefinic carbon atoms. The resulting dioxetane may decompose spontaneously, by heating above ambient temperature, usually below about 75° C., by reaction with acid or base, or by photo-activation in the absence or presence of a photosensitizer. Such linkages and reactions are described in the following exemplary references: U.S. Pat. Nos. 5,756,726; 5,800,999; and 5,886,238.

Exemplary cleavable linkages and their cleavage products are illustrated in Singh et al, U.S. patent publication 2003/0013126. The thiazole cleavable linkage, "—$CH_2$-thiazole-$(CH2)_n$-C(=O)—NH-protein," results in an molecular tag with the moiety "—$CH_2$—C(=O)—NH—CHO." Preferably, n is in the range of from 1 to 12, and more preferably, from 1 to 6. The oxazole cleavable linkage, "—$CH_2$-oxazole-$(CH2)_n$-C(=O)—NH-protein," results in an molecular tag with the moiety "—$CH_2$—C(=O)O—CHO." An olefin cleavable linkage is shown in connection with the binding compound embodiment "B-L-M-D," described above and with D being a detection moiety, such as a fluorescein dye. The olefin cleavable linkage may be employed in other embodiments also. Cleavage of the illustrated olefin linkage results in an molecular tag of the form: "R—(C=O)-M-D," where "R" may be any substituent within the general description of the molecular tags, E, provided above. Preferably, R is an electron-donating group, e.g. Ullman et al, U.S. Pat. No. 6,251,581; Smith and March, March's Advanced Organic Chemistry: Reactions, Mechanisms, and Structure, $5^{th}$ Edition (Wiley-Interscience, New York, 2001); and the like. More preferably, R is an electron-donating group having from 1-8 carbon atoms and from 0 to 4 heteroatoms selected from the group consisting of O, S, and N. In further preference, R is —$N(Q)_2$, —OQ, p-[$C_6H_4N(Q)_2$], furanyl, n-alkylpyrrolyl, 2-indolyl, or the like, where Q is alkyl or aryl. In further reference to the olefin cleavable linkage of the Singh et al reference, substituents "X" and "R" are equivalent to substituents "X" and "Y" of the above formula describing cleavable linkage, L. A preferred thioether cleavable linkage has the form "—$(CH_2)_2$—S—CH($C_6H_5$)C(=O)NH—$(CH_2)_n$—NH—," wherein n is in the range of from 2 to 12, and more preferably, in the range of from 2 to 6.

Molecular tag, E, in the present invention may comprise an electrophoric tag as described in the following references when separation of pluralities of molecular tags are carried out by gas chromatography or mass spectrometry: Zhang et al, Bioconjugate Chem., 13: 1002-1012 (2002); Giese, Anal. Chem., 2: 165-168 (1983); and U.S. Pat. Nos. 4,650,750; 5,360,819; 5,516,931; 5,602,273; and the like.

Molecular tag, E, is preferably a water-soluble organic compound that is stable with respect to the active species, especially singlet oxygen, and that includes a detection or reporter group. Otherwise, E may vary widely in size and structure. In one aspect, E has a molecular weight in the range of from about 50 to about 2500 daltons, more preferably, from about 50 to about 1500 daltons. Preferred structures of E are described more fully below. E may comprise a detection group for generating an electrochemical, fluorescent, or chromogenic signal. In embodiments employing detection by mass, E may not have a separate moiety for detection purposes. Preferably, the detection group generates a fluorescent signal.

In one aspect, molecular tag, E, is (M, D), where M is a mobility-modifying moiety and D is a detection moiety. The notation "(M, D)" is used to indicate that the ordering of the M and D moieties may be such that either moiety can be adjacent to the cleavable linkage, L. That is, "B-L-(M, D)" designates binding compound of either of two forms: "B-L-M-D" or "B-L-D-M."

Detection moiety, D, may be a fluorescent label or dye, a chromogenic label or dye, an electrochemical label, or the like. Preferably, D is a fluorescent dye. Exemplary fluorescent dyes for use with the invention include water-soluble rhodamine dyes, fluoresceins, 4,7-dichlorofluoresceins, benzoxanthene dyes, and energy transfer dyes, disclosed in the following references: Handbook of Molecular Probes and Research Reagents, $8^{th}$ ed., (Molecular Probes, Eugene, 2002); Lee et al, U.S. Pat. No. 6,191,278; Lee et al, U.S. Pat. No. 6,372,907; Menchen et al, U.S. Pat. No. 6,096,723; Lee et al, U.S. Pat. No. 5,945,526; Lee et al, Nucleic Acids Research, 25: 2816-2822 (1997); Hobb, Jr., U.S. Pat. No. 4,997,928; Khanna et al., U.S. Pat. No. 4,318,846; and the like. Preferably, D is a fluorescein or a fluorescein derivative.

The size and composition of mobility-modifying moiety, M, can vary from a bond to about 100 atoms in a chain, usually not more than about 60 atoms, more usually not more than about 30 atoms, where the atoms are carbon, oxygen, nitrogen, phosphorous, boron and sulfur. Generally, when other than a bond, the mobility-modifying moiety has from about 0 to about 40, more usually from about 0 to about 30 heteroatoms, which in addition to the heteroatoms indicated above may include halogen or other heteroatom. The total number of atoms other than hydrogen is generally fewer than about 200 atoms, usually fewer than about 100 atoms. Where acid groups are present, depending upon the pH of the medium in which the mobility-modifying moiety is present, various cations may be associated with the acid group. The acids may be organic or inorganic, including carboxyl, thionocarboxyl, thiocarboxyl, hydroxamic, phosphate, phosphite, phosphonate, phosphinate, sulfonate, sulfinate, boronic, nitric, nitrous, etc. For positive charges, substituents include amino (includes ammonium), phosphonium, sulfonium, oxonium, etc., where substituents are generally aliphatic of from about 1-6 carbon atoms, the total number of carbon atoms per heteroatom, usually be less than about 12, usually less than about 9. The side chains include amines, ammonium salts, hydroxyl groups, including phenolic groups, carboxyl groups, esters, amides, phosphates, heterocycles. M may be a homo-oligomer or a hetero-oligomer, having different monomers of the same or different chemical characteristics, e.g., nucleotides and amino acids.

Molecular tags within a plurality are selected so that each has a unique separation characteristic and/or a unique optical property with respect to the other members of the same plurality. In one aspect, the chromatographic or electrophoretic separation characteristic is retention time under set of standard separation conditions conventional in the art, e.g. voltage, column pressure, column type, mobile phase, electrophoretic separation medium, or the like. In another aspect, the optical property is a fluorescence property, such as emission spectrum, fluorescence lifetime, fluorescence intensity at a given wavelength or band of wavelengths, or the like. Preferably, the fluorescence property is fluorescence intensity. For example, each molecular tag of a plurality may have the same fluorescent emission properties, but each will differ from one another by virtue of a unique retention time. On the other hand, or two or more of the molecular tags of a plurality may have identical migration, or retention, times, but they will have unique fluorescent properties, e.g. spectrally resolvable emission spectra, so that all the members of the plurality are distinguishable by the combination of molecular separation and fluorescence measurement.

Preferably, molecular tags are separated by a techniques that is capable of providing quantitative information as well as qualitative information about the presence or absence of molecular tags (and therefore, corresponding analytes). In one aspect, a liquid phase separation technique is employed so that a solution, e.g. buffer solution, reaction solvent, or the like, containing a mixture of molecular tags is processed to bring about separation of individual kinds of molecular tags. Usually, such separation is accompanied by the differential movement of molecular tags from such a starting mixture along a path until discernable peaks or bands form that correspond to regions of increased concentration of the respective molecular tags. Such a path may be defined by a fluid flow, electric field, magnetic field, or the like. The selection of a particular separation technique depends on several factors including the expense and convenience of using the technique, the resolving power of the technique given the chemical nature of the molecular tags, the number of molecular tags to be separated, the type of detection mode employed, and the like. Preferably, molecular tags are electrophoretically separated to form an electropherogram in which the separated molecular tags are represented by distinct peaks.

Preferably, released molecular tags are detected by electrophoretic separation and the fluorescence of a detection group. In such embodiments, molecular tags having substantially identical fluorescence properties have different electrophoretic mobilities so that distinct peaks in an electropherogram are formed under separation conditions. Preferably, pluralities of molecular tags of the invention are separated by conventional capillary electrophoresis apparatus, either in the presence or absence of a conventional sieving matrix. Exemplary capillary electrophoresis apparatus include Applied Biosystems (Foster City, Calif.) models 310, 3100 and 3700; Beckman (Fullerton, Calif.) model P/ACE MDQ; Amersham Biosciences (Sunnyvale, Calif.) MegaBACE 1000 or 4000; SpectruMedix genetic analysis system; and the like. Electrophoretic mobility is proportional to $q/M^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01, and may be 0.02 or more. Preferably, in such conventional apparatus, the electrophoretic mobilities of molecular tags of a plurality differ by at least one percent, and more preferably, by at least a percentage in the range of from 1 to 10 percent. Further guidance for electrophoretic separation of molecular tags is given in the following references, which are incorporated by reference: Singh et al, U.S. patent publication US2003/0170915; and Williams et al, U.S. patent publication US2003/0170734.

Attaching Molecular Tags to Binding Moieties

Extensive guidance can be found in the literature for covalently linking molecular tags to binding compounds, such as antibodies, e.g. Hermanson, Bioconjugate Techniques, (Academic Press, New York, 1996), and the like. In one aspect of the invention, one or more molecular tags are attached directly or indirectly to common reactive groups on a binding compound. Common reactive groups include amine, thiol, carboxylate, hydroxyl, aldehyde, ketone, and the like, and may be coupled to molecular tags by commercially available cross-linking agents, e.g. Hermanson (cited above); Haugland, Handbook of Fluorescent Probes and Research Products, Ninth Edition (Molecular Probes, Eugene, Oreg., 2002). In one embodiment, an NHS-ester of a molecular tag is reacted with a free amine on the binding compound.

Figure 2A:
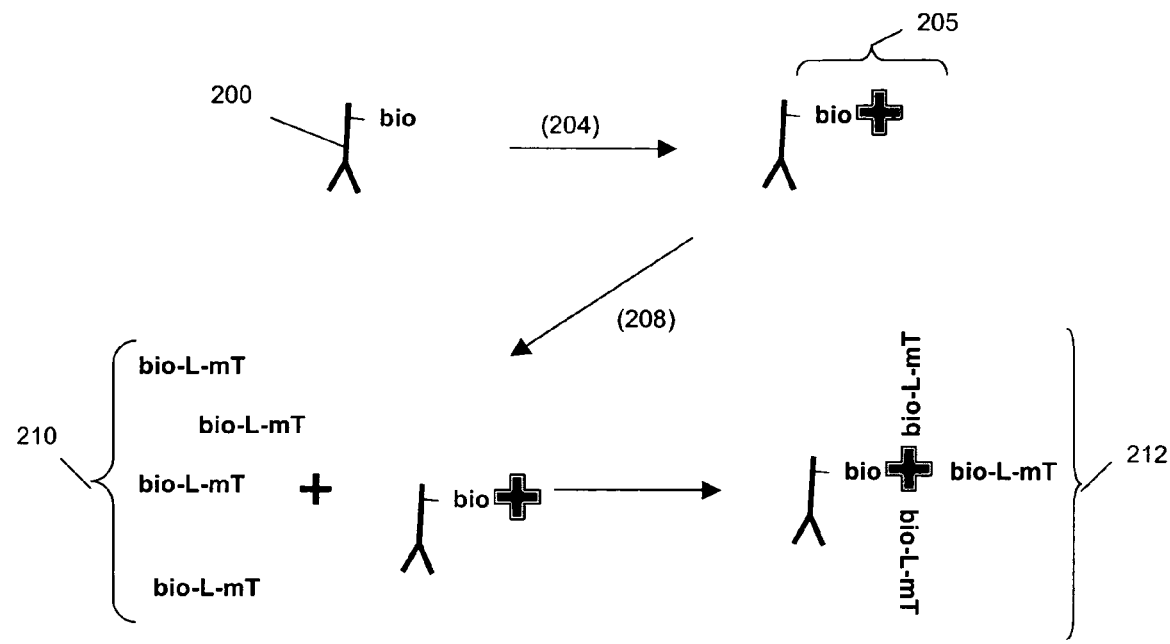
FIGS. 2A-2D illustrate diagrammatically methods for attaching molecular tags to antibodies.

In another embodiment illustrated in FIG. 2A, binding compounds comprise a biotinylated antibody (200) as a binding moiety. Molecular tags are attached to binding moiety (200) by way of avidin or streptavidin bridge (206). Preferably, in operation, binding moiety (200) is first reacted with a target complex, after which avidin or streptavidin is added (204) to form antibody-biotin-avidin complex (205). To such complexes (205) are added (208) biotinylated molecular tags (210) to form binding compound (212).

Figure 2B:
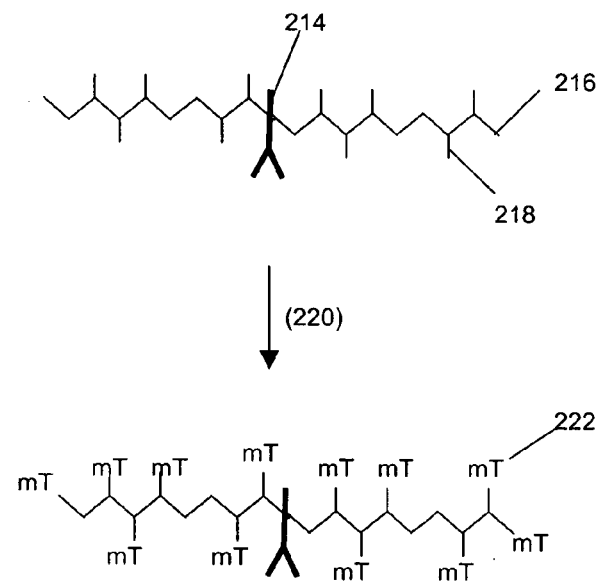

In still another embodiment illustrated in FIG. 2B, binding compounds comprise an antibody (214) derivatized with a multi-functional moiety (216) that contains multiple functional groups (218) that are reacted (220) molecular tag precursors to give a final binding compound having multiple molecular tags (222) attached. Exemplary multi-functional moieties include aminodextran, and like materials.

Once each of the binding compounds is separately derivatized by a different molecular tag, it is pooled with other binding compounds to form a plurality of binding compounds. Usually, each different kind of binding compound is present in a composition in the same proportion; however, proportions may be varied as a design choice so that one or a subset of particular binding compounds are present in greater or lower proportion depending on the desirability or requirements for a particular embodiment or assay. Factors that may affect such design choices include, but are not limited to, antibody affinity and avidity for a particular target, relative prevalence of a target, fluorescent characteristics of a detection moiety of a molecular tag, and the like.

Cleavage-Inducing Moiety Producing Active Species

A cleavage-inducing moiety, or cleaving agent, is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background because beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide, and the like. Illustrative quenchers for active species that cause oxidation include polyenes, carotenoids, vitamin E, vitamin C, amino acid-pyrrole N-conjugates of tyrosine, histidine, and glutathione, and the like, e.g. Beutner et al, Meth. Enzymol., 319: 226-241 (2000).

An important consideration for the cleavage-inducing moiety and the cleavable linkage is that they not be so far removed from one another when bound to a target protein that the active species generated by the sensitizer diffuses and loses its activity before it can interact with the cleavable linkage. Accordingly, a cleavable linkage preferably are within 1000 nm, preferably 20-200 nm of a bound cleavage-inducing moiety. This effective range of a cleavage-inducing moiety is referred to herein as its "effective proximity."

Generators of active species include enzymes, such as oxidases, such as glucose oxidase, xanthene oxidase, D-amino acid oxidase, NADH-FMN oxidoreductase, galactose oxidase, glyceryl phosphate oxidase, sarcosine oxidase, choline oxidase and alcohol oxidase, that produce hydrogen peroxide, horse radish peroxidase, that produces hydroxyl radical, various dehydrogenases that produce NADH or NADPH, urease that produces ammonia to create a high local pH.

A sensitizer is a compound that can be induced to generate a reactive intermediate, or species, usually singlet oxygen. Preferably, a sensitizer used in accordance with the invention is a photosensitizer. Other sensitizers included within the scope of the invention are compounds that on excitation by heat, light, ionizing radiation, or chemical activation will release a molecule of singlet oxygen. The best known members of this class of compounds include the endoperoxides such as 1,4-biscarboxyethyl-1,4-naphthalene endoperoxide, 9,10-diphenylanthracene-9,110-endoperoxide and 5,6,11,12-tetraphenyl naphthalene 5,12-endoperoxide. Heating or direct absorption of light by these compounds releases singlet oxygen. Further sensitizers are disclosed in the following references: Di Mascio et al, FEBS Lett., 355: 287 (1994) (peroxidases and oxygenases); Kanofsky, J. Biol. Chem. 258: 5991-5993 (1983)(lactoperoxidase); Pierlot et al, Meth. Enzymol., 319: 3-20 (2000)(thermal lysis of endoperoxides); and the like.

The cleavage-inducing moiety may be associated with the support by being covalently or non-covalently attached to the surface of the support or incorporated into the body of the support. Linking to the surface may be accomplished as discussed above. The cleavage-inducing moiety may be incorporated into the body of the support either during or after the preparation of the support. In general, the cleavage-inducing moiety is associated with the support in an amount necessary to achieve the necessary amount of active species. Generally, the amount of cleavage-inducing moiety is determined empirically.

As mentioned above, the preferred cleavage-inducing moiety in accordance with the present invention is a photosensitizer that produces singlet oxygen. As used herein, "photosensitizer" refers to a light-adsorbing molecule that when activated by light converts molecular oxygen into singlet oxygen. Photosensitizers may be attached directly or indirectly, via covalent or non-covalent linkages, to the binding agent of a class-specific reagent. Guidance for constructiing of such compositions, particularly for antibodies as binding agents, available in the literature, e.g. in the fields of photodynamic therapy, immunodiagnostics, and the like. The following are exemplary references: Ullman, et al., Proc. Natl. Acad. Sci. USA 91, 5426-5430 (1994); Strong et al, Ann. New York Acad. Sci., 745: 297-320 (1994); Yarmush et al, Crit. Rev. Therapeutic Drug Carrier Syst., 10: 197-252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516,636; and the like.

A large variety of light sources are available to photoactivate photosensitizers to generate singlet oxygen. Both polychromatic and monchromatic sources may be used as long as the source is sufficiently intense to produce enough singlet oxygen in a practical time duration. The length of the irradiation is dependent on the nature of the photosensitizer, the nature of the cleavable linkage, the power of the source of irradiation, and its distance from the sample, and so forth. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include, by way of illustration and not limitation, lasers such as, e.g., helium-neon lasers, argon lasers, YAG lasers, He/Cd lasers, and ruby lasers; photodiodes; mercury, sodium and xenon vapor lamps; incandescent lamps such as, e.g., tungsten and tungsten/halogen; flashlamps; and the like. By way of example, a photoactivation device disclosed in Bjornson et al, International patent publication WO 03/051669 is employed. Briefly, the photoactivation device is an array of light emitting diodes (LEDs) mounted in housing that permits the simultaneous illumination of all the wells in a 96-well plate. A suitable LED for use in the present invention is a high power GaAlAs IR emitter, such as model OD-880W manufactured by OPTO DIODE CORP. (Newbury Park, Calif.).

Examples of photosensitizers that may be utilized in the present invention are those that have the above properties and are enumerated in the following references: Singh and Ullman, U.S. Pat. No. 5,536,834; Li et al, U.S. Pat. No. 5,763, 602; Martin et al, Methods Enzymol., 186: 635-645 (1990); Yarmush et al, Crit. Rev. Therapeutic Drug Carrier Syst., 10: 197-252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516,636; Thetford, European patent publ. 0484027; Sessler et al, SPIE, 1426: 318-329 (1991); Magda et al, U.S. Pat. No. 5,565,552; Roelant, U.S. Pat. No. 6,001,673; and the like.

Figure 2C:
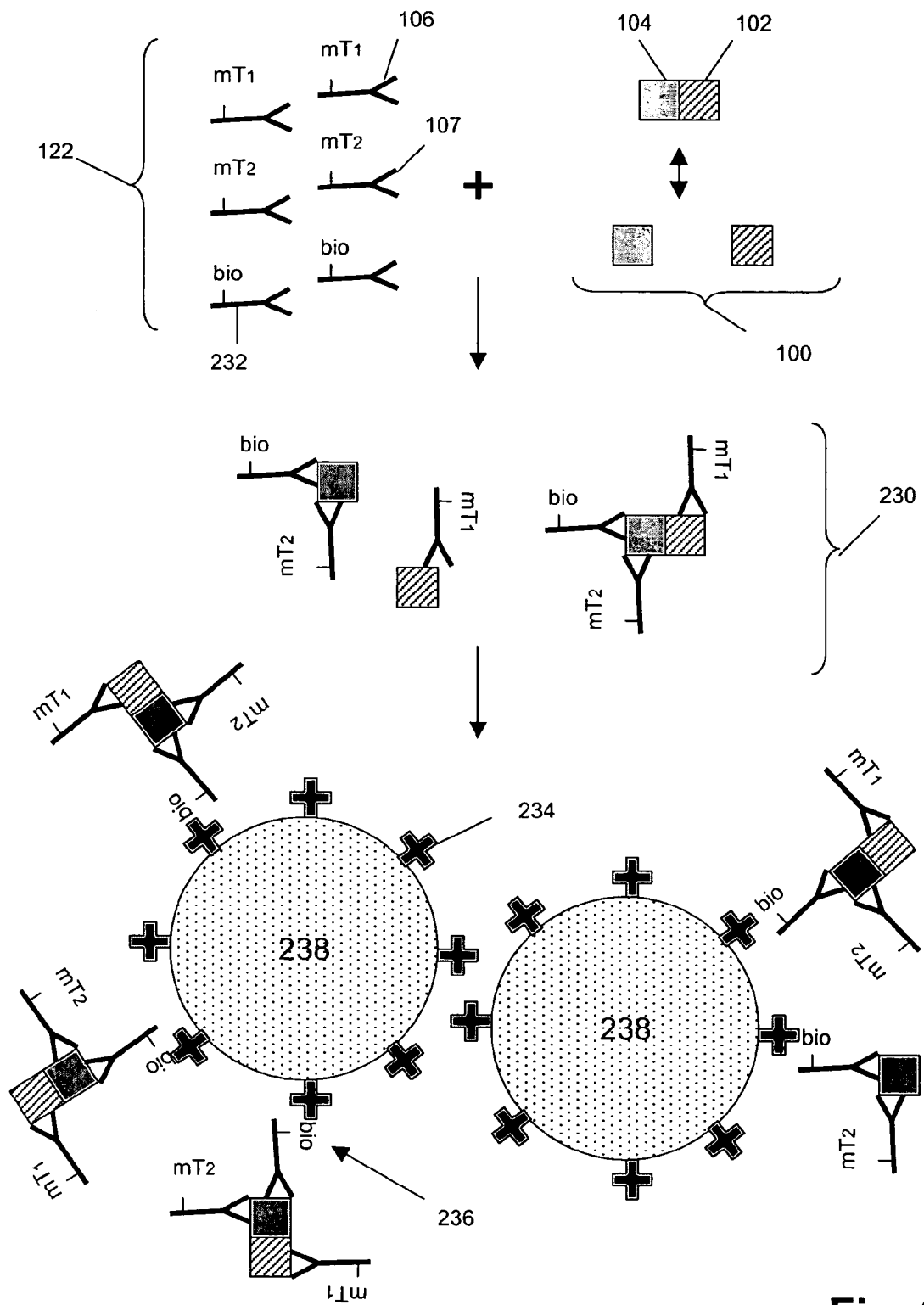
Figure 2D:
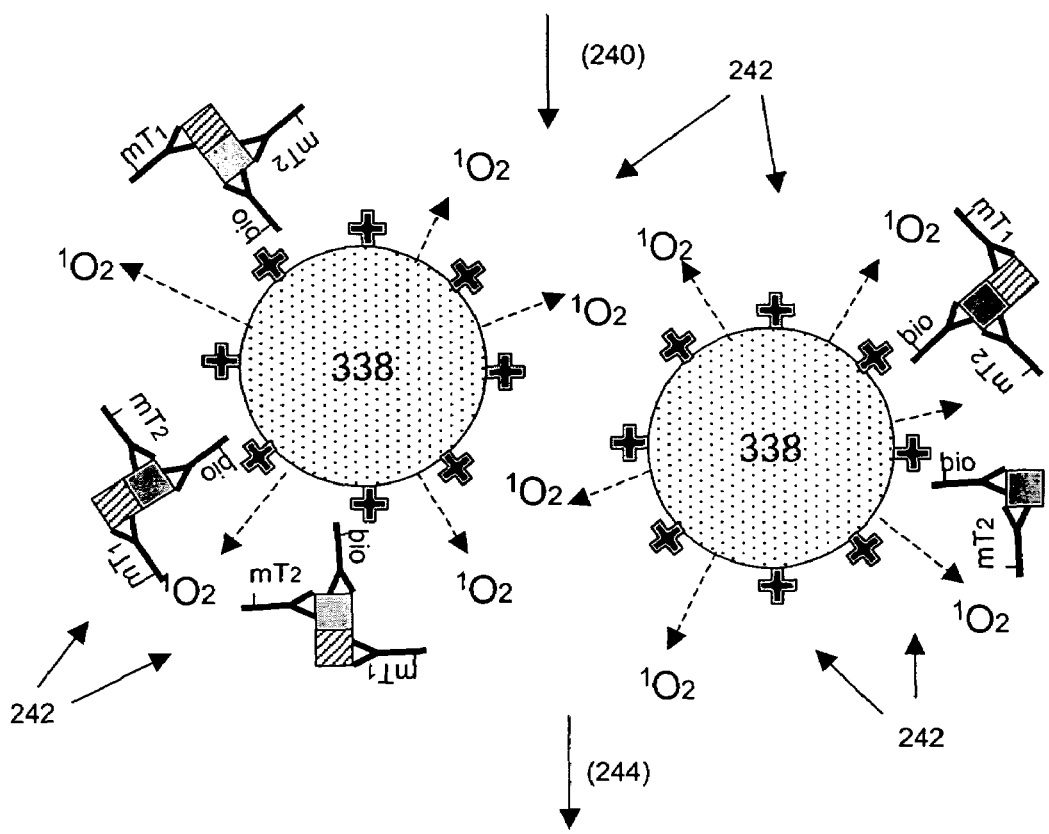
Figure 2D:
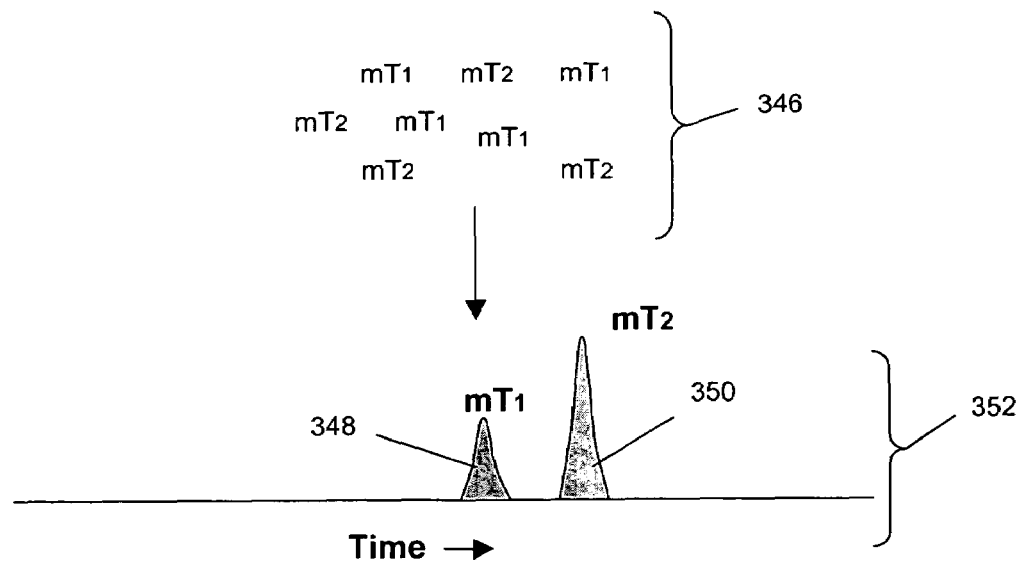

As with sensitizers, in certain embodiments, a photosensitizer may be associated with a solid phase support by being covalently or non-covalently attached to the surface of the support or incorporated into the body of the support. In general, the photosensitizer is associated with the support in an amount necessary to achieve the necessary amount of singlet oxygen. Generally, the amount of photosensitizer is determined empirically. In one preferred embodiment, a photosensitizer is incorporated into a latex particle to form photosensitizer beads, e.g. as disclosed by Pease et al., U.S. Pat. No. 5,709,994; Pollner, U.S. Pat. No. 6,346,384; and Pease et al, PCT publication WO 01/84157. Use of such photosensitizer beads is illustrated in FIG. 2C. As described in FIG. 1B for heteroduplex detection, complexes (230) are formed after combining reagents (122) with a sample. In this case, instead of attaching a photosensitizer directly to a binding compound, such as an antibody, a cleaving probe comprises two components: antibody (232) derivatized with a capture moiety, such as biotin (indicated in FIG. 2C as "bio") and photosensitizer bead (238) whose surface is derivatized with an agent (234) that specifically binds with the capture moiety, such as avidin or streptavidin. Complexes (230) are then captured (236) by photosensitizer beads by way of the capure moiety. After an appropriate buffer for separation has been added, if necessary, photosensitizer beads (238) are illuminated so that singlet oxygen is generated (242) and molecular tags are released (244). Such released molecular tags (246) are then separated to form separation profile (252) and dimers are quantified ratiometrically from peaks (248) and (250). Photosensitizer beads may be used in either homogeneous or heterogeneous assay formats.

Figure 3:
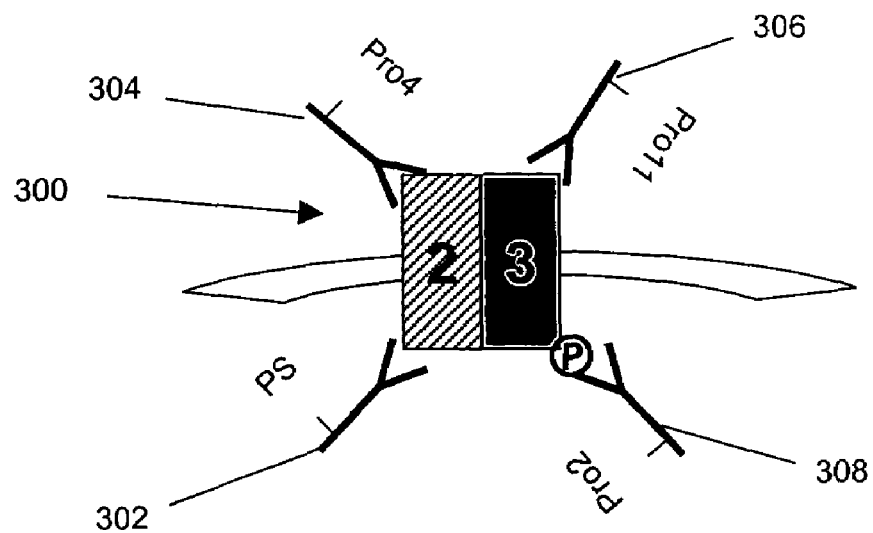
FIG. 3 illustrates diagrammatically an assay for detecting receptor dimers in lysates of enriched cell populations.

In one embodiment, a photosensitizer is incorporated into a latex particle to form photosensitizer beads, e.g. as disclosed by Pease et al., U.S. Pat. No. 5,709,994; Pollner, U.S. Pat. No. 6,346,384; and Pease et al, PCT publication WO 01/84157. Alternatively, photosensitizer beads may be prepared by covalently attaching a photosensitizer, such as rose bengal, to 0.5 micron latex beads by means of chloromethyl groups on the latex to provide an ester linking group, as described in J. Amer. Chem. Soc., 97: 3741 (1975). Use of such photosensitizer beads is illustrated in FIG. 3C. As described in FIG. 1C for heteroduplex detection, complexes (330) are formed after combining reagents (1122) with a sample. This reaction may be carried out, for example, in a conventional 96-well or 384-well microtiter plate, or the like, having a filter membrane that forms one wall, e.g. the bottom, of the wells that allows reagents to be removed by the application of a vacuum. This allows the convenient exchange of buffers, if the buffer required for specific binding of binding compounds is different that the buffer required for either singlet oxygen generation or separation. For example, in the case of antibody-based binding compounds, a high salt buffer is required. If electrophoretic separation of the released tags is employed, then better performance is achieved by exchanging the buffer for one that has a lower salt concentration suitable for electrophoresis. In this embodiment, instead of attaching a photosensitizer directly to a binding compound, such as an antibody, a cleaving probe comprises two components: antibody (332) derivatized with a capture moiety, such as biotin (indicated in FIG. 3C as "bio") and photosensitizer bead (338) whose surface is derivatized with an agent (334) that specifically binds with the capture moiety, such as avidin or streptavidin. Complexes (330) are then captured (335) by photosensitizer beads by way of the capture moiety, such as biotin (336). Conveniently, if the pore diameter of the filter membrane is selected so that photosensitizer beads (338) cannot pass, then a buffer exchange also serves to remove unbound binding compounds, which leads to an improved signal. After an appropriate buffer for separation has been added, if necessary, photosensitizer beads (338) are illuminated so that singlet oxygen is generated (342) and molecular tags are released (344). Such released molecular tags (346) are then separated to form separation profile (352) and dimers are quantified ratiometrically from peaks (348) and (350). Photosensitizer beads may be used in either homogeneous or heterogeneous assay formats.

In another exemplary embodiment, the photosensitizer rose bengal is covalently attached to 0.5 micron latex beads by means of chloromethyl groups on the latex to provide an ester linking group, as described in J. Amer. Chem. Soc., 97: 3741 (1975).

Exemplary Cells and Antigens

The types of rare circulating cells that may be detected by the method of the invention vary widely and include virtually any cell type that possesses a biomarker and a capture antigen. Of particular interest are fetal cells and metastatic cancer cells. For cancer cells many capture antigens are known for which antibodies are available for use in an immunomagnetic enrichment step. Using breast cancer as an example, such antibodies may include anti-MUC-1, anti-estrogen receptor, anti-progesterone receptor, anti-CA27.29, anti-CA15.5, anti-cathepsin D, anti-p53, anti-urokinase type plasminogen activator, anti-epidermal growth factor, anti-epidermal growth factor receptor, anti-BRCA1, anti-BRCA2, anti-prostate specific antigen, anti-plasminogen activator inhibitor and/or anti-Her1, anti-Her2, anti-Her3, or anti-Her4 antibodies. Additional markers for aggressiveness and invasiveness are Lewis a (Lea), sialyl Lewis a (sLea), the intergrins (CD49b, CD49c, CD29), gelatinase A and B (MMP-2, MMP-9), tissue collagenase (MMP-1), fibroblast activation protein (FAP), guanidinobenzoatase, CEA, S100 family (S100A4, mtsl, 18A2/mtsl, pEL-98, p9Ka, metastasin), the Cyclins A and E, p27, p53, vascular endothelilal growth factor (VGEF) and E-Cadherin.

Preferably, cancer biomarkers comprise receptor dimers, especially RTK receptor dimers, and/or intracellular protein-protein complexes associated with signal transduction pathways. Examples of such dimers and complexes are listed in the table below.

TABLE II

Exemplary RTK Dimers and Intracellular Complexes (here "protein 1//protein 2" indicates a complex comprising protein 1 and protein 2)

| RTK Dimer | Downstream Complexes |
|---|---|
| Her1-Her1 | Her1//Shc, Grb2//Sos, Her1//Grb7, Her1//RasGAP |
| Her1-Her2 | Her1//Shc, Grb2//Shc, Her2//Shc, Grb2//Sos, 14-3-3//Bad, Her1//RasGAP |
| Her1-Her3 | Her3//PI3K, Her3//Shc, Her3//Grb7, Her1//Shc, Grb2//Sos, 14-3-3//Bad, Her1//RasGAP |
| Her1-Her4 | Her3//PI3K, Her1//Shc, Grb2//Sos, Her1//RasGAP |
| Her2-Her2 | Her2//Shc, Grb2//Sos, 14-3-3//Bad, Her1//RasGAP |
| Her2-Her3 | Her3//PI3K, Her3//Shc, Her3//Grb7, Grb2//Shc, Her2//Shc, Grb2//Sos, 14-3-3//Bad, Her1//RasGAP |
| Her2-Her4 | Her3//PI3K, Grb2//Shc, Her2//Shc, Grb2//Sos, 14-3-3//Bad; YAP//Her4, Her1//RasGAP |
| Her3-Her4 | Her3//PI3K, Her3//Shc, Her3//Grb7, YAP//Her4, Her1//RasGAP |
| Her4-Her4 | Her3//PI3K, YAP//Her4, Her1//RasGAP |
| IGF-1R (covalent homodimers) | IGF-1R//PI3K, IGF-1R//Shc; IGFR//IRS1 |
| VEGFR1(Flt1)-VEGFR2(KDR) | VEGFR//Shc; VEGFR//PI(3)K; VEGFR//Src; VEGFR//FRS2 |
| VEGFR2(KDR)-VEGFR2(KDR) | VEGFR//Shc; VEGFR//PI(3)K; VEGFR//Src; VEGFR//FRS2 |
| PDGFRa-PDGFRa | PDGFRa//Crk, PDGFR//Grb2; PDGFR//Grb7; PDGFR//Nck; PDGFR//Shc; , PDGFR//STAT5 |
| PDGFRa-PDGFRb | PDGFRa//Crk, PDGFRb//GAP, PDGFR//Grb2; PDGFR//Grb7; PDGFR//Nck; PDGFR//Shc, PDGFR//Shp2; PDGFR//RasGAP, PDGFR//STAT5 |
| PDGFRb-PDGFRb | PDGFRb//GAP, PDGFR//Grb2; PDGFR//Grb7; PDGFR//Nck; PDGFR//Shc, PDGFR//Shp2, PDGFR//RasGAP; , PDGFR//STAT5 |
| Kit/SCFR(homodimers) | Kit//Shp-1; Kit//p85PI(3)K; Kit//Grb2; Kit//CRKL |
| FGFR (particularly FGFR1 homodimers) | FGFR//PLCg1; FGFR//Crk; FGFR//FRS2; FGFR//Shp2; FGFR//Shb |
| NGFR(TrkA)-NGFR(TrkA) | Trk//p75NTR; Trk//PI(3)K Shc//Grb2; Grb2//SOS Shc//Her1; Shc//Her2; Shc//Her3; PI3K//Her1; IGF-1R//PI3K; IGF-1R//Shc; Erk//Rsk; 14-3-3//FKHRL1; Cyclin D1//Cdk4; 14-3-3//tuberin; 14-3-3//Cdc25C; 14-3-3σ//Cdc2; RXRα//CAR; RXRα//PPARα; RXRα//PXR; Hsp90//Akt1 |

Assay Conditions

The following general discussion of methods and specific conditions and materials are by way of illustration and not limitation. One of ordinary skill in the art will understand how the methods described herein can be adapted to other applications, particularly with using different samples, cell types and target complexes.

In conducting the methods of the invention, a combination of the assay components is made, including the sample being tested, the binding compounds, and optionally the cleaving probe. Generally, assay components may be combined in any order. In certain applications, however, the order of addition may be relevant. For example, one may wish to monitor competitive binding, such as in a quantitative assay. Or one may wish to monitor the stability of an assembled complex. In such applications, reactions may be assembled in stages, and may require incubations before the complete mixture has been assembled, or before the cleaving reaction is initiated.

The amounts of each reagent are usually determined empirically. The amount of sample used in an assay will be determined by the predicted number of target complexes present and the means of separation and detection used to monitor the signal of the assay. In general, the amounts of the binding compounds and the cleaving probe are provided in molar excess relative to the expected amount of the target molecules in the sample, generally at a molar excess of at least 1.5, more desirably about 10-fold excess, or more. In specific applications, the concentration used may be higher or lower, depending on the affinity of the binding agents and the expected number of target molecules present on a single cell. Where one is determining the effect of a chemical compound on formation of oligomeric cell surface complexes, the compound may be added to the cells prior to, simultaneously with, or after addition of the probes, depending on the effect being monitored.

The assay mixture is combined and incubated under conditions that provide for binding of the probes to the cell surface molecules, usually in an aqueous medium, generally at a physiological pH (comparable to the pH at which the cells are cultures), maintained by a buffer at a concentration in the range of about 10 to 200 mM. Conventional buffers may be used, as well as other conventional additives as necessary, such as salts, growth medium, stabilizers, etc. Physiological and constant temperatures are normally employed. Incubation temperatures normally range from about 4° to 70° C., usually from about 15° to 45° C., more usually 25° to 37°.

After assembly of the assay mixture and incubation to allow the probes to bind to cell surface molecules, the mixture is treated to activate the cleaving agent to cleave the tags from the binding compounds that are within the effective proximity of the cleaving agent, releasing the corresponding tag from the cell surface into solution. The nature of this treatment will depend on the mechanism of action of the cleaving agent. For example, where a photosensitizer is employed as the cleaving agent, activation of cleavage will comprise irradiation of the mixture at the wavelength of light appropriate to the particular sensitizer used.

Following cleavage, the sample is then analyzed to determine the identity of tags that have been released. Where an assay employing a plurality of binding compounds is employed, separation of the released tags will generally precede their detection. The methods for both separation and detection are determined in the process of designing the tags for the assay. A preferred mode of separation employs electrophoresis, in which the various tags are separated based on known differences in their electrophoretic mobilities.

EXAMPLE 1

Analysis of Cell Lysates for Her-2 Heterodimerization and Receptor Phosphorylation on Magnetically Isolated Circulating Cells In this example, Her1-Her2 and Her2-Her3 heterodimers and phosphorylation states are measured in cell lysates from an enriched population of cells from a test blood sample. The test blood sample is made by spiking normal blood with known numbers of the tumor cell line MCF-7 (about 500 cells/mL normal blood). The enriched population is treated with various concentrations of epidermal growth factor (EGF) and heregulin (HRG) then assayed using the binding compounds and a cleaving probe as described below.

Sample Preparation:
1. 10 mL of test sample blood is incubated with the anti-Her3 conjugated ferrofluid for 15 minutes. The tubes are placed into a separator composed of four opposing magnets for 10 minutes (CellTracks AutoPrep System, Immunicon, Huntingdon Valley, Pa.). After separation, the blood is aspirated and discarded. The tube is taken out of the magnetic separator and the collected fraction is resuspended from the walls of the vessel.
2. Serum-starve enriched population of cells overnight before use.
3. Stimulate cell lines with EGF and/or HRG in culture media for 10 minutes at 37° C. Exemplary doses of EGF/HRG are 0, 0.032, 0.16, 0.8, 4, 20, 100 nM.
4. Aspirate culture media, transfer onto ice, and add lysis buffer to lyse cells in situ.
5. Scrape and transfer lysate to microfuge tube. Incubate on ice for 30 min. Microfuge at 14,000 rpm, 4° C., for 10 min. (Centrifugation is optional.)
6. Collect supernatants as lysates and aliquot for storage at −80° C. until use.

Assay design: As illustrated diagrammatically in FIG. 3, Her2-Her3 heterodimers (300) are quantified ratiometrically based on the binding of cleaving probe (302) and binding compounds (304), (306), and (308). A similar assay is also constructed for Her1-Her2 dimers. A photosensitizer indicated by "PS" is attached to cleaving probe (302) via an avidin-biotin linkage, and binding compounds (304), (306), and (308) are labeled with molecular tags Pro4, Pro11, and Pro2, respectively. Binding compound (304) is specific for a phosphorylation site on Her3. Molecular tags Pro4, Pro11, and Pro2 are disclosed in Singh et al, U.S. patent publication 2003/0013126, which is incorporated by reference.

The total assay volume is 40 ul. The lysate volume is adjusted to 30 ul with lysis buffer. The antibodies are diluted in lysis buffer up to 10 ul. Typically ~5000 to 15000 cell-equivalent of lysates is used per reaction. The detection limit is ~1000 cell-equivalent of lysates.

Procedure: Final concentrations of pre-mixed binding compounds (i.e. molecular tag- or biotin-antibody conjugates) in reaction:
Pro4_anti-Her-2: 0.1 ug/ml
Pro10_Ab11 anti-Her-1: 0.05-0.1 ug/ml
Pro11_anti-Her-3: 0.1 ug/ml
Pro2_PT100 anti-phospho-Tyr: 0.1 ug/ml
Biotin_anti-Her-2: 1-2 ug/ml
1. To assay 96-well, add 10 ul antibody mix to 30 ul lysate and incubate for 1 hour at RT.
2. Add 2 ul streptavidin-derivatized cleaving probe (final 2 ug/well) to assay well and incubate for 45 min.
3. Add 150 ul of PBS with 1% BSA to 96-well filter plate (Millipore MAGVN2250) and incubate for 1 hr at RT for blocking.
4. Empty filter plate by vacuum suction. Transfer assay reactions to filter plate and apply vacuum to empty.
5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 min.
8. Transfer 10 ul of each reaction to CE assay plate for analysis using an ABI3100 CE instrument with a 22 cm capillary (injection conditions: 5 kV, 75 sec, 30° C.; run conditions: 600 sec, 30° C.).

Assay buffers are as follows:

| Lysis Buffer (made fresh and stored on ice) | | |
|---|---|---|
| Final | ul | Stock |
| 1% Triton X-100 | 1000 | 10% |
| 20 mM Tris-HCl (pH 7.5) | 200 | 1 M |
| 100 mM NaCl | 200 | 5 M |
| 50 mM NaF | 500 | 1 M |
| 50 mM Na beta-glycerophosphate | 1000 | 0.5 M |
| 1 mM $Na_3VO_4$ | 100 | 0.1 M |
| 5 mM EDTA | 100 | 0.5 M |
| 10 ug/ml pepstatin | 100 | 1 mg/ml |
| 1 tablet (per 10 ml) Roche Complete protease inhibitor (#1836170) | N/A | N/A |
| Water | 6500 | N/A |
| | 10 ml | Total |

| Wash buffer (stored at 4° C.) | | |
|---|---|---|
| Final | ml | Stock |
| 1% NP-40 | 50 | 10% |
| 1x PBS | 50 | 10x |
| 150 mM NaCl | 15 | 5 M |
| 5 mM EDTA | 5 | 0.5 M |
| Water | 380 | N/A |
| | 500 ml | Total |

| Illumination buffer: | | |
|---|---|---|
| Final | ul | Stock |
| 0.005x PBS | 50 | 1x |
| CE std | 3 | 100x |
| 10 mM Tris-HCl (pH 8.0) | | 0.1 M |

-continued

| Illumination buffer: | | |
|---|---|---|
| Final | ul | Stock |
| 10 pM A160 | | 1 nM |
| 10 pM A315 | | 1 nM |
| 10 pM HABA | | 1 nM |
| Water | 10,000 | N/A |
| | 10 ml | Total |

Data Analysis:
1. Normalize relative fluorescence units (RFU) signal of each molecular tag against CE reference standard A315.
2. Subtract RFU of "no lysate" background control from corresponding molecular tag signals.
3. Report heterodimerization for Her-1 or Her-3 as the corresponding RFU ratiometric to RFU from Pro4_anti-Her-2 from assay wells using biotin-anti-Her-2.
4. Report receptor phosphorylation for Her-1,2,3 as RFU from Pro2_PT100 anti-phospho-Tyr ratiometric to RFU from Pro4_anti-Her-2 from assay wells using biotin-anti-Her-2.

What is claimed is:

1. A method of detecting one or more protein-protein complexes of a rare cell type in a sample containing a mixed population of cells such that each protein-protein complex has a first protein and a second protein, the method comprising:
   immunomagnetically isolating from the sample a subpopulation of cells containing the rare cell type with one or more antibody compositions, wherein each antibody composition is specific for a cell surface antigen of the rare cell type and wherein each antibody composition is attached to a magnetic particle;
   combining with the subpopulation of cells
   (a) one or more different first binding compounds specific for each first protein of each of the one or more protein-protein complexes of the rare cell type, wherein each first binding compound has one or more molecular tags attached thereto via a cleavable linkage, the one or more molecular tags of each different binding compound having a distinct separation characteristic so that the one or more molecular tags of each different binding compound form distinct peaks in a separation profile upon separation; and
   (b) one or more different second binding compounds specific for each second protein of each of the one or more protein-protein complexes of the rare cell type, wherein each second binding compound is conjugated to a cleaving-inducing moiety having an effective proximity;
   wherein each of the first binding compounds specifically binds to each first protein and each of the second binding compounds specifically binds to each second protein, and wherein the one or more molecular tags of each first binding compound are released; and
   separating and identifying the released by the cleaving-inducing moiety when in effective proximity to said one or more molecular tags molecular tags to detect the one or more protein-protein complexes in the sample.

2. The method of claim 1 wherein said protein-protein complex is a receptor dimer.

3. The method of claim 2 wherein said predetermined separation characteristic is electrophoretic mobility.

4. The method of claim 2 wherein said receptor dimer comprises one or more ErbB receptors.

5. The method of claim 4 wherein said protein-protein complex is selected from the group consisting or Her1//Shc, Her2//Shc, Her3//Shc, Her3/PI3K, and IGF-1R//PI3K.

6. The method of claim 1, wherein the rare cell type is a cancer cell.

7. The method of claim 1, wherein the rare cell type is a fetal cell.

8. The method of claim 1, wherein the sample is a patient sample.

9. The method of claim 1, wherein the sample is a biological sample.

10. The method of claim 9, wherein the biological sample is a culture, blood, saliva, cerebral spinal fluid, pleural fluid, milk, lymph, sputum, semen, needle aspirate sample.

11. The method of claim 10, wherein the biological sample is a blood sample.

* * * * *

UNITED STATES PATENT AND TRADEMARK OFFICE
CERTIFICATE OF CORRECTION

PATENT NO. : 7,537,938 B2
APPLICATION NO. : 10/765773
DATED : May 26, 2009
INVENTOR(S) : Hrair Kirakossian et al.

It is certified that error appears in the above-identified patent and that said Letters Patent is hereby corrected as shown below:

Column 32, line 18, claim 1 after "molecular tags," delete "molecular tags".

Signed and Sealed this

Eighth Day of December, 2009

David J. Kappos
*Director of the United States Patent and Trademark Office*